US012629446B2

(12) United States Patent
Kobayashi et al.

(10) Patent No.: US 12,629,446 B2
(45) Date of Patent: May 19, 2026

(54) VASCULAR EMBOLIC SYSTEM

(71) Applicant: 3-D Matrix, Ltd., Newton, MA (US)

(72) Inventors: Satoru Kobayashi, Chigasaki (JP);
Kentaro Takamura, Tokyo (JP)

(73) Assignee: 3-D Matrix, Ltd., Tokyo (JP)

( * ) Notice: Subject to any disclaimer, the term of this
patent is extended or adjusted under 35
U.S.C. 154(b) by 0 days.

(21) Appl. No.: 19/235,902

(22) Filed: Jun. 12, 2025

(65) Prior Publication Data

US 2025/0311587 A1      Oct. 2, 2025

Related U.S. Application Data

(63) Continuation of application No. 17/535,470, filed on
Nov. 24, 2021, now abandoned, which is a
continuation of application No. 14/442,677, filed as
application No. PCT/IB2013/060145 on Nov. 14,
2013, now abandoned.

(60) Provisional application No. 61/726,250, filed on Nov.
14, 2012.

(51) Int. Cl.
| | |
|---|---|
| *A61L 24/10* | (2006.01) |
| *A61B 6/00* | (2024.01) |
| *A61B 6/50* | (2024.01) |
| *A61B 17/12* | (2006.01) |
| *A61K 49/04* | (2006.01) |
| *A61L 24/00* | (2006.01) |
| *A61L 31/04* | (2006.01) |
| *A61M 5/00* | (2006.01) |
| *C07K 7/08* | (2006.01) |
| *H10K 59/60* | (2023.01) |

(52) U.S. Cl.
CPC ............ *A61L 24/108* (2013.01); *A61B 6/481*
(2013.01); *A61B 6/504* (2013.01); *A61B*
*17/12186* (2013.01); *A61K 49/0438* (2013.01);
*A61L 24/0031* (2013.01); *A61L 31/047*
(2013.01); *C07K 7/08* (2013.01); *H10K 59/60*
(2023.02); *A61B 17/12109* (2013.01); *A61B*
*17/12113* (2013.01); *A61L 2400/04* (2013.01);
*A61L 2400/06* (2013.01); *A61L 2430/36*
(2013.01); *A61M 5/007* (2013.01)

(58) Field of Classification Search
None
See application file for complete search history.

(56) References Cited

U.S. PATENT DOCUMENTS

| | | |
|---|---|---|
| 7,179,784 B2 | 2/2007 | Zhang |
| 7,449,180 B2 | 11/2008 | Kisiday |
| 7,671,258 B2 | 3/2010 | Zhang |
| 7,713,923 B2 | 5/2010 | Genove |
| 8,022,178 B2 | 9/2011 | Horii et al. |
| 8,299,032 B2 | 10/2012 | Yokoi |
| 8,647,867 B2 | 2/2014 | Kobayashi |
| 8,729,032 B2 | 5/2014 | Nagai et al. |
| 8,741,833 B2 | 6/2014 | Kumada |
| 8,901,084 B2 | 12/2014 | Genove |
| 9,011,879 B2 | 4/2015 | Seward |
| 9,012,404 B2 | 4/2015 | Spirio et al. |
| 9,084,837 B2 | 7/2015 | Ellis-Behnke et al. |
| 9,162,005 B2 | 10/2015 | Ellis-Behnke et al. |
| 9,327,010 B2 | 5/2016 | Ellis-Behnke et al. |
| 9,339,476 B2 | 5/2016 | Norchi et al. |
| 9,364,513 B2 | 6/2016 | Ellis-Behnke et al. |
| 9,415,084 B2 | 8/2016 | Ellis-Behnke et al. |
| 9,439,941 B2 | 9/2016 | Ellis-Behnke et al. |
| 9,724,448 B2 | 8/2017 | Kobayashi et al. |
| 2005/0208138 A1 * | 9/2005 | Yang .................. A61K 31/717 604/500 |
| 2006/0084607 A1 | 4/2006 | Spirio et al. |
| 2009/0053276 A1 | 2/2009 | Richard |
| 2010/0143504 A1 | 6/2010 | Spirio et al. |
| 2010/0158849 A1 | 6/2010 | Khatri et al. |
| 2010/0215613 A1 | 8/2010 | Shibutani et al. |
| 2011/0117195 A1 | 5/2011 | Hsieh et al. |
| 2011/0201541 A1 * | 8/2011 | Takamura ................ A61P 7/04 530/326 |
| 2012/0123355 A1 | 5/2012 | Delap et al. |
| 2013/0281547 A1 | 10/2013 | Spirio et al. |
| 2014/0038909 A1 | 2/2014 | Takamura et al. |
| 2014/0329914 A1 | 11/2014 | Kobayashi |
| 2015/0105336 A1 | 4/2015 | Takamura et al. |

(Continued)

FOREIGN PATENT DOCUMENTS

| | | |
|---|---|---|
| CN | 102170919 | 8/2011 |
| EP | 2345433 | 7/2011 |

(Continued)

OTHER PUBLICATIONS

Brazilian Office Action in Brazilian Application No. 1120150227473,
dated Jul. 22, 2019, 6 pages (with English translation).
European Call Minutes in European Application No. 13802115.9,
dated Nov. 7, 2019, 4 pages.
European Office Action in European Application No. 13802115.9,
dated Jun. 11, 2018, 6 pages.
Kumar et al, "Coil occlusion of the large patent ductus arteriosus."
Images in paediatric cardiology, Jan. 2008, 10(1):8.
Stuart "Chemoembolization in the Management of Liver Tumors,"
The Oncologist, Oct. 1, 2003, 8(5):425-437.
Walsh, "Advanced Embolization Techniques." Pediatric Cardiol-
ogy, 2005, 26(3):275-288.

(Continued)

*Primary Examiner* — Sudhakar Katakam
*Assistant Examiner* — Zachary J Miknis
(74) *Attorney, Agent, or Firm* — IP Supra, PLLC;
Constantine Linnik; Beth L. Smiley

(57) ABSTRACT

Systems and methods of blocking a biological vessel are
provided. The systems and methods may comprise intro-
ducing to the vessel an amphiphilic peptide. The peptide
may comprise at least thirteen amino acids that may alter-
nate between a hydrophobic amino acid and a hydrophilic
amino acid. The peptide may form a beta-sheet spontane-
ously in an aqueous solution in the presence of a cation.

9 Claims, 9 Drawing Sheets

Specification includes a Sequence Listing.

(56) References Cited

U.S. PATENT DOCUMENTS

| | | |
|---|---|---|
| 2015/0197359 A1 | 7/2015 | Nohara et al. |
| 2016/0000966 A1 | 1/2016 | Kobayashi et al. |
| 2016/0015855 A1 | 1/2016 | Nohara et al. |
| 2016/0030628 A1 | 2/2016 | Kobayashi |
| 2016/0287744 A1 | 10/2016 | Kobayashi et al. |
| 2016/0317607 A1 | 11/2016 | Spirio et al. |
| 2016/0362451 A1 | 12/2016 | Gil et al. |
| 2017/0072008 A1 | 3/2017 | Mehta et al. |
| 2017/0128172 A1 | 5/2017 | Spirio et al. |
| 2017/0128622 A1 | 5/2017 | Spirio et al. |
| 2017/0173105 A1 | 6/2017 | Mehta et al. |
| 2017/0173221 A1 | 6/2017 | Mehta et al. |
| 2017/0202986 A1 | 7/2017 | Gil et al. |
| 2017/0312370 A1 | 11/2017 | Otsuka et al. |
| 2018/0023049 A1 | 1/2018 | Gil et al. |

FOREIGN PATENT DOCUMENTS

| | | |
|---|---|---|
| EP | 2345433 A1 | 7/2011 |
| JP | 10-127754 A | 5/1998 |
| JP | 2007-37989 A | 2/2007 |
| JP | 2010-083788 A | 4/2010 |
| JP | 2012-511055 A | 5/2012 |
| JP | 2012211185 | 11/2012 |
| WO | 2006014570 A2 | 2/2006 |
| WO | WO2006014570 | 2/2006 |
| WO | WO2006116524 | 11/2006 |
| WO | WO2008039483 | 4/2008 |
| WO | WO2010041636 | 4/2010 |
| WO | WO 2009072556 | 4/2011 |
| WO | 2011092196 A1 | 8/2011 |
| WO | 2013030673 A2 | 3/2013 |
| WO | WO2014076660 | 5/2014 |

OTHER PUBLICATIONS

Anonymous: "European Neurological Devices Market", XP055254147, Retrieved from the Internet: URL: http://idataresearch.com/eu ropean-neu rological-devices-marketresearch-repo rt-2012/ [retrieved on Mar. 1, 2016].

Correa et al. 'A graph-structural method for prediction of polymer properties' Brazilian Journal of Chemical Engineering v21 (4) Oct.-Dec. 2004 pp. 621-628.

International Search Report in International Application No. PCT/IB2013/060145, dated Jan. 31, 2014.

EP Granted Claims (App. No. EP 13802115.9) identified as "Main Request".

Decision of the Board of Appeal, dated Feb. 6, 2024, App. No. EP 13802115.9.

Decision to grant a European Patent, dated May 15, 2025, in EP Application No. 13802115.9 (filed Jun. 12, 2025 in this Application file).

Arai, Tomoyuki—Declaration Under 37 C.F.R. Sec. 1.137(a), dated Dec. 18, 2020 (filed Jun. 12, 2025 in this Application file; filed previously in parent and grandparent U.S. Applications).

Anonymous (3-D Matrix, Ltd.), "Shared Research Report on 3-D Matrix, Ltd." Jun. 22, 2012.

Fornell, D. "The Basics of Guide Wire Technology," Diagnostics and Interventional Cardiology, Mar. 18, 2011.

Iqbal et al. "Patent Ductus Arteriosus Device Embolization," Images Paediatric Cardiology (2011) 13(1): 1-5.

Chvapil et al. "A Standardized Animal Model for Evaluation of Hemostatic Effectiveness of Various Materials," J. of Trauma: Injury, Infection, and Critical Care (1983) 23:1042-1047.

Gastroenterological Surgery Nursing, vol. 13, No. 10, pp. 39-42 (2008).

Anonymous, "European Neurological Devices Market," Dec. 31, 2012; XP055254147, Retrieved from the Internet: URL: http://idataresearch.com/european-neurological-devices-marketresearch-report-2012/ [retrieved on Mar. 1, 2016] (reference D3).

Kumar, RK and Nair, AC "Coil Occlusion of the Large Patent Ductus Arteriosus," Images Pediatr. Cardiol. (2008) 10(1): 8-26—(reference D6).

Stuart, K "Chemoembolization in the Management of Liver Tumors," The Oncologist (2003) 8: 425-437 (reference D4).

Walsh, KP "Advanced Embolization Techniques," Pediatric Cardiol. (2005) 26: 275-288—(reference D5).

Wang, T. et al. "Molecular Mechanisms of RADA16-1 Peptide on Fast Stop Bleeding in Rat Models," Intl. J. Mol. Sci. (2012) 13: 15279-15290; doi:10.3390/ijms131115279—(reference D7—being filed herewith).

Pfizer, Gelfoam USP, Feb. 2012.

University of Wisconsin-Madison, Research Animal Resources and Compliance; https://www.rarc.wisc.edu/tools_and_guides/techniques/ rodent_blood_collection.html [accessed Jun. 5, 2023].

Iwamoto, Shozo "Transcatheter arterial chemoembolization (TACE)," Gastroenterological Surgery Nursing (2008) 13(10): 39-42 (in Japanese with English translation provided).

Loffroy et al. "Endovascular Therapeutic Embolisation: An Overview of Occluding Agents and their Effects on Embolised Tissues," Current Vascular Pharmacology (2009) 7: 250-263.

Notice of Reasons for Refusal, dated Sep. 3, 2025, in sister JP App. No. 2021-114234 to 3-D Matrix, Ltd. (is machine translation).

* cited by examiner

Left Kidney Before Embolization

Left Kidney After Embolization

SEQUENCE LISTING

```
Sequence total quantity: 58
SEQ ID NO: 1            moltype = AA  length = 4
FEATURE                Location/Qualifiers
REGION                 1..4
                       note = source = /note="Description of Artificial Sequence:
                        Synthetic peptide"
source                 1..4
                       mol_type = protein
                       organism = synthetic construct
SEQUENCE: 1
RADA                                                          4

SEQ ID NO: 2            moltype = AA  length = 200
FEATURE                Location/Qualifiers
VARIANT                9..200
                       note = /replace=" "
REGION                 1..200
                       note = misc_feature - /note="This sequence many encompass
                        2-50 'Arg-Ala-Asp-Ala' repeating units"
REGION                 1..200
                       note = misc_feature - /note="Variant residues given in the
                        sequence have no preference with respect to those in the
                        annotations for variant positions"
REGION                 1..200
                       note = source = /note="Description of Artificial Sequence:
                        Synthetic polypeptide"
source                 1..200
                       mol_type = protein
                       organism = synthetic construct
SEQUENCE: 2
RADARADARA DARADARADA RADARADARA DARADARADA RADARADARA DARADARADA  60
RADARADARA DARADARADA RADARADARA DARADARADA RADARADARA DARADARADA  120
RADARADARA DARADARADA RADARADARA DARADARADA RADARADARA DARADARADA  180
RADARADARA DARADARADA                                             200
```

-continued

```
SEQ ID NO: 3          moltype = AA  length = 4
FEATURE               Location/Qualifiers
REGION                1..4
                      note = source = /note="Description of Artificial Sequence:
                       Synthetic peptide"
source                1..4
                      mol_type = protein
                      organism = synthetic construct
SEQUENCE: 3
IEIK                                                                   4

SEQ ID NO: 4          moltype = AA  length = 200
FEATURE               Location/Qualifiers
VARIANT               9..200
                      note = /replace=" "
REGION                1..200
                      note = misc_feature - /note="This sequence many encompass
                       2-50 'Ile-Glu-Ile-Lys' repeating units"
REGION                1..200
                      note = misc_feature - /note="Variant residues given in the
                       sequence have no preference with respect to those in the
                       annotations for variant positions"
REGION                1..200
                      note = source = /note="Description of Artificial Sequence:
                       Synthetic polypeptide"
source                1..200
                      mol_type = protein
                      organism = synthetic construct
SEQUENCE: 4
IEIKIEIKIE IKIEIKIEIK IEIKIEIKIE IKIEIKIEIK IEIKIEIKIE IKIEIKIEIK   60
IEIKIEIKIE IKIEIKIEIK IEIKIEIKIE IKIEIKIEIK IEIKIEIKIE IKIEIKIEIK  120
IEIKIEIKIE IKIEIKIEIK IEIKIEIKIE IKIEIKIEIK IEIKIEIKIE IKIEIKIEIK  180
IEIKIEIKIE IKIEIKIEIK                                              200

SEQ ID NO: 5          moltype = AA  length = 4
FEATURE               Location/Qualifiers
REGION                1..4
                      note = source = /note="Description of Artificial Sequence:
                       Synthetic peptide"
source                1..4
                      mol_type = protein
                      organism = synthetic construct
SEQUENCE: 5
KLDL                                                                   4

SEQ ID NO: 6          moltype = AA  length = 200
FEATURE               Location/Qualifiers
VARIANT               9..200
                      note = /replace=" "
REGION                1..200
                      note = misc_feature - /note="This sequence many encompass
                       2-50 'Lys-Leu-Asp-Leu' repeating units"
REGION                1..200
                      note = misc_feature - /note="Variant residues given in the
                       sequence have no preference with respect to those in the
                       annotations for variant positions"
REGION                1..200
                      note = source = /note="Description of Artificial Sequence:
                       Synthetic polypeptide"
source                1..200
                      mol_type = protein
                      organism = synthetic construct
SEQUENCE: 6
KLDLKLDLKL DLKLDLKLDL KLDLKLDLKL DLKLDLKLDL KLDLKLDLKL DLKLDLKLDL   60
KLDLKLDLKL DLKLDLKLDL KLDLKLDLKL DLKLDLKLDL KLDLKLDLKL DLKLDLKLDL  120
KLDLKLDLKL DLKLDLKLDL KLDLKLDLKL DLKLDLKLDL KLDLKLDLKL DLKLDLKLDL  180
KLDLKLDLKL DLKLDLKLDL                                              200

SEQ ID NO: 7          moltype = AA  length = 16
FEATURE               Location/Qualifiers
REGION                1..16
                      note = source = /note="Description of Artificial Sequence:
                       Synthetic peptide"
source                1..16
                      mol_type = protein
                      organism = synthetic construct
SEQUENCE: 7
RADARADARA DARADA                                                    16
```

-continued

```
SEQ ID NO: 8          moltype = AA  length = 13
FEATURE               Location/Qualifiers
REGION                1..13
                      note = source = /note="Description of Artificial Sequence:
                      Synthetic peptide"
source                1..13
                      mol_type = protein
                      organism = synthetic construct
SEQUENCE: 8
IEIKIEIKIE IKI                                                            13

SEQ ID NO: 9          moltype = AA  length = 17
FEATURE               Location/Qualifiers
REGION                1..17
                      note = source = /note="Description of Artificial Sequence:
                      Synthetic peptide"
source                1..17
                      mol_type = protein
                      organism = synthetic construct
SEQUENCE: 9
IEIKIEIKIE IKIEIKI                                                        17

SEQ ID NO: 10         moltype = AA  length = 12
FEATURE               Location/Qualifiers
REGION                1..12
                      note = source = /note="Description of Artificial Sequence:
                      Synthetic peptide"
source                1..12
                      mol_type = protein
                      organism = synthetic construct
SEQUENCE: 10
KLDLKLDLKL DL                                                             12

SEQ ID NO: 11         moltype = AA  length = 16
FEATURE               Location/Qualifiers
REGION                1..16
                      note = source = /note="Description of Artificial Sequence:
                      Synthetic peptide"
source                1..16
                      mol_type = protein
                      organism = synthetic construct
SEQUENCE: 11
AEAEAKAKAE AEAKAK                                                         16

SEQ ID NO: 12         moltype = AA  length = 16
FEATURE               Location/Qualifiers
REGION                1..16
                      note = source = /note="Description of Artificial Sequence:
                      Synthetic peptide"
source                1..16
                      mol_type = protein
                      organism = synthetic construct
SEQUENCE: 12
KAKAKAKAKA KAKAKA                                                         16

SEQ ID NO: 13         moltype = AA  length = 5
FEATURE               Location/Qualifiers
REGION                1..5
                      note = source = /note="Description of Artificial Sequence:
                      Synthetic peptide"
source                1..5
                      mol_type = protein
                      organism = synthetic construct
SEQUENCE: 13
KAKAK                                                                     5

SEQ ID NO: 14         moltype = AA  length = 16
FEATURE               Location/Qualifiers
REGION                1..16
                      note = source = /note="Description of Artificial Sequence:
                      Synthetic peptide"
source                1..16
                      mol_type = protein
                      organism = synthetic construct
SEQUENCE: 14
AKAKAEAEAK AKAEAE                                                         16

SEQ ID NO: 15         moltype = AA  length = 16
FEATURE               Location/Qualifiers
```

-continued

```
REGION                  1..16
                        note = source = /note="Description of Artificial Sequence:
                         Synthetic peptide"
source                  1..16
                        mol_type = protein
                        organism = synthetic construct
SEQUENCE: 15
AKAEAKAEAK AEAKAE                                                          16

SEQ ID NO: 16           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 16
AEAEAKAK                                                                   8

SEQ ID NO: 17           moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 17
AEAKAEAEAK AK                                                              12

SEQ ID NO: 18           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 18
KAEAKAEAKA EAKAEA                                                          16

SEQ ID NO: 19           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 19
AEAKAEAKAE AKAEAK                                                          16

SEQ ID NO: 20           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 20
ARARADAD                                                                   8

SEQ ID NO: 21           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 21
ADADARARAD ADARAR                                                          16

SEQ ID NO: 22           moltype = AA  length = 16
FEATURE                 Location/Qualifiers
```

```
REGION                  1..16
                        note = source = /note="Description of Artificial Sequence:
                         Synthetic peptide"
source                  1..16
                        mol_type = protein
                        organism = synthetic construct
SEQUENCE: 22
ARADARADAR ADARAD                                                     16

SEQ ID NO: 23           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 23
DARADARADA RADARA                                                     16

SEQ ID NO: 24           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 24
ADARADARAD ARADAR                                                     16

SEQ ID NO: 25           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 25
ARARADADAR ARADAD                                                     16

SEQ ID NO: 26           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 26
ARADAKAEAR ADAKAE                                                     16

SEQ ID NO: 27           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 27
AKAEARADAK AEARAD                                                     16

SEQ ID NO: 28           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 28
ARAKADAEAR AKADAE                                                     16

SEQ ID NO: 29           moltype = AA  length = 16
FEATURE                 Location/Qualifiers
```

-continued

```
REGION                1..16
                      note = source = /note="Description of Artificial Sequence:
                       Synthetic peptide"
source                1..16
                      mol_type = protein
                      organism = synthetic construct
SEQUENCE: 29
AKARAEADAK ARADAE                                                          16

SEQ ID NO: 30         moltype = AA  length = 16
FEATURE               Location/Qualifiers
REGION                1..16
                      note = source = /note="Description of Artificial Sequence:
                       Synthetic peptide"
source                1..16
                      mol_type = protein
                      organism = synthetic construct
SEQUENCE: 30
AQAQAQAQAQ AQAQAQ                                                          16

SEQ ID NO: 31         moltype = AA  length = 16
FEATURE               Location/Qualifiers
REGION                1..16
                      note = source = /note="Description of Artificial Sequence:
                       Synthetic peptide"
source                1..16
                      mol_type = protein
                      organism = synthetic construct
SEQUENCE: 31
VQVQVQVQVQ VQVQVQ                                                          16

SEQ ID NO: 32         moltype = AA  length = 16
FEATURE               Location/Qualifiers
REGION                1..16
                      note = source = /note="Description of Artificial Sequence:
                       Synthetic peptide"
source                1..16
                      mol_type = protein
                      organism = synthetic construct
SEQUENCE: 32
YQYQYQYQYQ YQYQYQ                                                          16

SEQ ID NO: 33         moltype = AA  length = 16
FEATURE               Location/Qualifiers
REGION                1..16
                      note = source = /note="Description of Artificial Sequence:
                       Synthetic peptide"
source                1..16
                      mol_type = protein
                      organism = synthetic construct
SEQUENCE: 33
HQHQHQHQHQ HQHQHQ                                                          16

SEQ ID NO: 34         moltype = AA  length = 16
FEATURE               Location/Qualifiers
REGION                1..16
                      note = source = /note="Description of Artificial Sequence:
                       Synthetic peptide"
source                1..16
                      mol_type = protein
                      organism = synthetic construct
SEQUENCE: 34
ANANANANAN ANANAN                                                          16

SEQ ID NO: 35         moltype = AA  length = 16
FEATURE               Location/Qualifiers
REGION                1..16
                      note = source = /note="Description of Artificial Sequence:
                       Synthetic peptide"
source                1..16
                      mol_type = protein
                      organism = synthetic construct
SEQUENCE: 35
VNVNVNVNVN VNVNVN                                                          16

SEQ ID NO: 36         moltype = AA  length = 16
FEATURE               Location/Qualifiers
```

-continued

```
REGION                  1..16
                        note = source = /note="Description of Artificial Sequence:
                         Synthetic peptide"
source                  1..16
                        mol_type = protein
                        organism = synthetic construct
SEQUENCE: 36
YNYNYNYNYN YNYNYN                                                    16

SEQ ID NO: 37           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 37
HNHNHNHNHN HNHNHN                                                    16

SEQ ID NO: 38           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 38
ANAQANAQAN AQANAQ                                                    16

SEQ ID NO: 39           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 39
AQANAQANAQ ANAQAN                                                    16

SEQ ID NO: 40           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 40
VNVQVNVQVN VQVNVQ                                                    16

SEQ ID NO: 41           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 41
VQVNVQVNVQ VNVQVN                                                    16

SEQ ID NO: 42           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 42
YNYQYNYQYN YQYNYQ                                                    16

SEQ ID NO: 43           moltype = AA  length = 16
FEATURE                 Location/Qualifiers
```

-continued

```
REGION                  1..16
                        note = source = /note="Description of Artificial Sequence:
                         Synthetic peptide"
source                  1..16
                        mol_type = protein
                        organism = synthetic construct
SEQUENCE: 43
YQYNYQYNYQ YNYQYN                                                16

SEQ ID NO: 44           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 44
HNHQHNHQHN HQHNHQ                                                16

SEQ ID NO: 45           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 45
HQHNHQHNHQ HNHQHN                                                16

SEQ ID NO: 46           moltype = AA  length = 18
FEATURE                 Location/Qualifiers
REGION                  1..18
                        note = source = /note="Description of Artificial Sequence:
                         Synthetic peptide"
source                  1..18
                        mol_type = protein
                        organism = synthetic construct
SEQUENCE: 46
AKAQADAKAQ ADAKAQAD                                              18

SEQ ID NO: 47           moltype = AA  length = 18
FEATURE                 Location/Qualifiers
REGION                  1..18
                        note = source = /note="Description of Artificial Sequence:
                         Synthetic peptide"
source                  1..18
                        mol_type = protein
                        organism = synthetic construct
SEQUENCE: 47
VKVQVDVKVQ VDVKVQVD                                              18

SEQ ID NO: 48           moltype = AA  length = 18
FEATURE                 Location/Qualifiers
REGION                  1..18
                        note = source = /note="Description of Artificial Sequence:
                         Synthetic peptide"
source                  1..18
                        mol_type = protein
                        organism = synthetic construct
SEQUENCE: 48
YKYQYDYKYQ YDYKYQYD                                              18

SEQ ID NO: 49           moltype = AA  length = 18
FEATURE                 Location/Qualifiers
REGION                  1..18
                        note = source = /note="Description of Artificial Sequence:
                         Synthetic peptide"
source                  1..18
                        mol_type = protein
                        organism = synthetic construct
SEQUENCE: 49
HKHQHDHKHQ HDHKHQHD                                              18

SEQ ID NO: 50           moltype = AA  length = 28
FEATURE                 Location/Qualifiers
```

-continued

```
REGION                  1..28
                        note = source = /note="Description of Unknown: Beta-amyloid
                         peptide"
source                  1..28
                        mol_type = protein
                        organism = unidentified
SEQUENCE: 50
DAEFRHDSGY EVHHQKLVFF AEDVGSNK                                            28

SEQ ID NO: 51           moltype = AA  length = 11
FEATURE                 Location/Qualifiers
REGION                  1..11
                        note = source = /note="Description of Unknown: Beta-amyloid
                         peptide"
source                  1..11
                        mol_type = protein
                        organism = unidentified
SEQUENCE: 51
GSNKGAIIGL M                                                              11

SEQ ID NO: 52           moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 52
RPKQQFGLM                                                                 9

SEQ ID NO: 53           moltype = AA  length = 11
FEATURE                 Location/Qualifiers
MOD_RES                 1
                        note = D-Arg
MOD_RES                 7
                        note = D-Trp
MOD_RES                 9
                        note = D-Trp
REGION                  1..11
                        note = source = /note="Description of Artificial Sequence:
                         Synthetic peptide"
source                  1..11
                        mol_type = protein
                        organism = synthetic construct
SEQUENCE: 53
RPKPQQWFWL L                                                              11

SEQ ID NO: 54           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 54
VRVRVDVDVR VRVDVD                                                         16

SEQ ID NO: 55           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 55
ADADAKAKAD ADAKAK                                                         16

SEQ ID NO: 56           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
```

-continued

```
SEQUENCE: 56
EAEAEAEAEA EAEAEA                                                    16

SEQ ID NO: 57          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 57
ADADADADAD ADADAD                                                    16

SEQ ID NO: 58          moltype = AA   length = 16
FEATURE                Location/Qualifiers
REGION                 1..16
                       note = source = /note="Description of Artificial Sequence:
                        Synthetic peptide"
REGION                 1..16
                       note = source = /note="N-term acetylated"
REGION                 1..16
                       note = source = /note="C-term amidated"
source                 1..16
                       mol_type = protein
                       organism = synthetic construct
SEQUENCE: 58
RADARADARA DARADA                                                    16
```

VASCULAR EMBOLIC SYSTEM

CONTINUITY

This application is a continuation of U.S. application Ser. No. 17/535,470, filed Nov. 24, 2021, which is a continuation of U.S. application Ser. No. 14/442,677, filed May 13, 2015, which is a National Stage entry of International Application No. PCT/IB2013/060145, filed Nov. 14, 2013, which claims priority to U.S. Provisional Application No. 61/726,250, filed Nov. 14, 2012, each of which is incorporated by reference herein in their entirety.

SEQUENCE LISTING

The instant application contains an XML Sequence Listing which has been submitted electronically and is hereby incorporated by reference in its entirety. Said Sequence Listing, created on Jun. 5, 2025, is named 3DMJP-X0001-US03_SequenceListing.xml and is 83,616 bytes in size.

FIELD OF THE DISCLOSURE

This disclosure relates to macroscopic membranes that may be used in medical, research, and industrial applications. More particularly, this disclosure relates to membranes, hydrogels, compositions and solutions that may be used in a vascular embolic system and embolization procedures. The vascular embolic system may provide an approach to at least partially block biological pathways or channels including vessels, veins, portal veins, arteries, and ducts that may transport blood and other fluids, such as lymph fluids.

SUMMARY

A method of blocking a biological vessel in a subject is provided. The method comprises introducing a catheter into a biological vessel and positioning an end of the catheter in a target area of the biological vessel in which at least a partial obstruction is desired. The method further comprises administering through the catheter a solution comprising an amphiphilic peptide comprising at least 12 amino acids that alternate between a hydrophobic amino acid and a hydrophilic amino acid in an effective amount and in an effective concentration to form a hydrogel under physiological conditions to allow at least partial blockage of the biological vessel. The method further comprises removing the catheter from the biological vessel with the at least partial obstruction in place.

A kit for blocking a biological vessel in a subject is provided. The kit comprises a solution comprising an amphiphilic peptide comprising at least 12 amino acids that alternate between a hydrophobic amino acid and a hydrophilic amino acid in an effective amount and in an effective concentration to form a hydrogel under physiological conditions to allow at least partial blockage of the biological vessel. The kit further comprises instructions for administering the solution to the biological vessel in the subject.

A method of facilitating blocking a biological vessel in a subject is provided. The method comprises providing a solution comprising an amphiphilic peptide comprising at least 12 amino acids that alternate between a hydrophobic amino acid and a hydrophilic amino acid in an effective amount and in an effective concentration to form a hydrogel under physiological conditions to allow at least partial blockage of the biological vessel. The method further comprises providing instructions for administering the solution to a target area of the biological vessel through introduction of the solution to a catheter positioned in the biological vessel.

BRIEF DESCRIPTION OF THE DRAWING

The accompanying drawings are not intended to be drawn to scale. For purposes of clarity, not every component may be labeled.

In the drawings.

DETAILED DESCRIPTION

Figure 1:
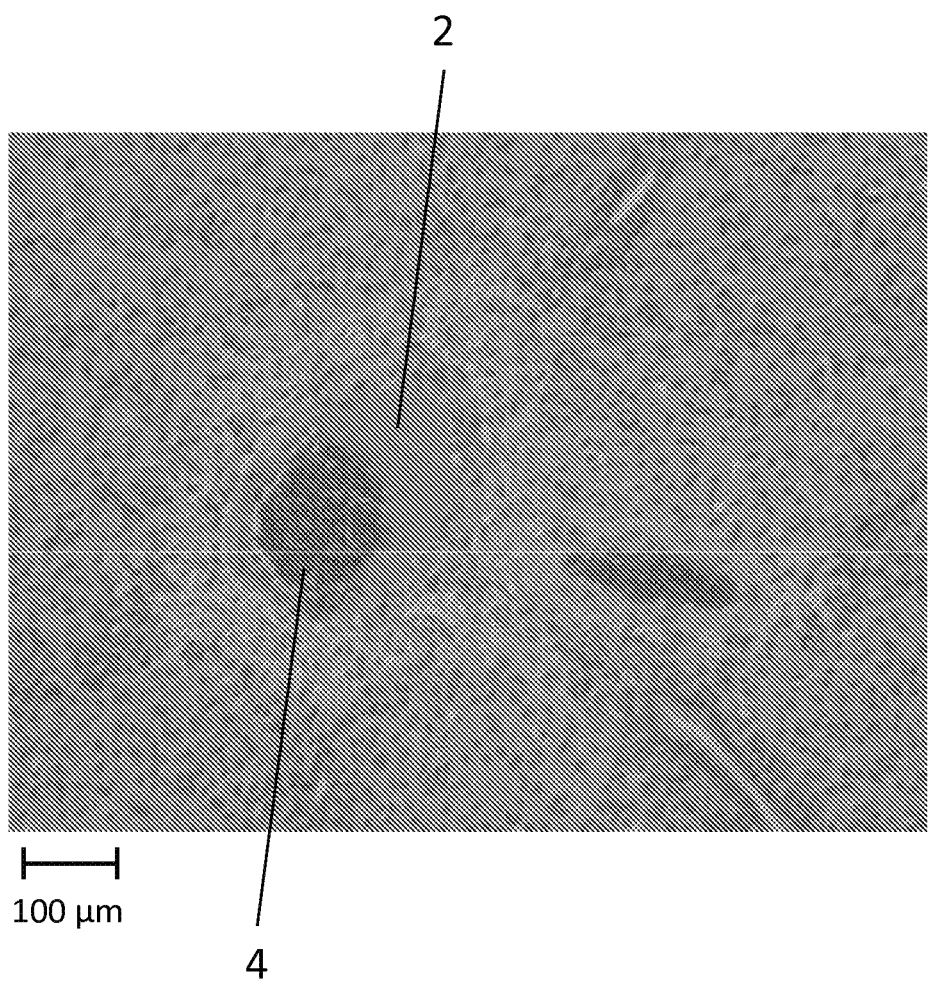
FIG. 1 is an image of a cross-section of a portal vein embolism using a peptide solution of the present disclosure.

Embolization is a procedure that creates a blockage, lodging, occlusion, or embolism in one or more biological pathways or channels. The biological pathways or channels may include vessels, veins, portal veins, arteries, and ducts that may transport blood and other fluids, such as lymph fluids. Embolization is used to treat a wide variety of conditions affecting different organs of a subject's body, including the human body. The one or more vessels may be targeted to purposely prevent or reduce the circulation of blood to a desired target. The embolization procedure may be used to purposely create such a blockage, lodging or occlusion in order to deprive tumors or other pathological processes of their blood supply (perfusion). Embolization may be used to treat disorders, malformations, or congenital ailments in biological vessels. For example, embolization may be used to treat patent ductus arteriosus (PDA). The embolization treatment may be used to treat major aortopulmonary collateral artery (MAPCA), recurrent hemotysis, arteriovenous malformations, cerebral aneurysms, gastrointestinal bleeding, epistaxis, post-partum hemorrhage, surgical hemorrhage, and uterine fibroids.

Embolization may be accomplished by several different techniques. It may be accomplished by administering a material, such as a liquid to a desired or predetermined location, such as a target area. Administering may include applying or injecting a material, such as a liquid to a desired or predetermined location, such as a target area.

Embolization may be used to shut down or block all or a portion of a vessel which forms an aneurysm in order to prevent the aneurysm from rupturing. Embolization may also be used to shut down or block all or a portion of certain blood vessels that surround a region of a subject that is being operated on, for example, during surgery of cerebral arteriovenous malformation (AVM).

Obstructing materials may be used to create a blockage or occlusion in a biological vessel to accomplish embolization. Obstructing materials may include metal coils, collagens, cyanoacrylates, and other materials. The materials may be inserted or placed at the desired surgical sites with the use of a catheter. Balloons may also be implanted in a target vessel and filled with saline.

Metal coils may remain in vivo permanently, but the safety of these coils in long-term applications is unknown. The metal coils may also result in incompatibility with magnetic devices. Collagens may have biological incompatabilities and cyanoacrylates may become toxic in vivo.

Specific liquid embolization agents may include onyx, n-butyl-2-cyanoacrylate (nbca) and ethiodol, made from iodine, poppyseed oil. Schlerosing agents, which harden the endothelial lining of vessels may also be used. Examples of such agents include ethanol, ethanolamine oleate and sotradecol. Particulate embolization agents include polyvinyl alcohol and acrylic gelatin microspheres.

The present disclosure provides for methods of embolizing or blocking biological vessels, methods of facilitating blocking a biological vessel, and kits for use in blocking a biological vessel. Biological vessels may include blood vessels and lymph ducts. Blood vessels may include arteries, veins, portal veins and capillaries. The term vascular may refer to biological vessels, including arteries, veins, portal veins, capillaries, and ducts.

The methods may comprise blocking or obstructing a biological vessel in a subject or methods of facilitating blocking or obstructing a biological vessel in a subject. As used herein, the term "subject" is intended to include human and non-human animals, for example, vertebrates, large animals, and primates. In certain embodiments, the subject is a mammalian subject, and in particular embodiments, the subject is a human subject. Although applications with humans are clearly foreseen, veterinary applications, for example, with non-human animals, are also envisaged herein. The term "non-human animals" of the invention includes all vertebrates, for example, non-mammals (such as birds, for example, chickens; amphibians; reptiles) and mammals, such as non-human primates, domesticated, and agriculturally useful animals, for example, sheep, dog, cat, cow, pig, rat, among others.

The embolism, blockage or obstruction may be partial or complete. By complete it is meant that the embolism, blockage or obstruction prevents substantially all blood flow past the embolism, blockage, or obstruction. The systems and methods may include administration, application, or injection of a self-assembling peptide, or a solution comprising a self-assembling peptide, to a predetermined or desired target area. The self-assembling peptide may be applied or introduced to a biological vessel in the form of a self-assembling peptide solution, hydrogel, membrane or other form.

The self-assembling peptide solution may be an aqueous self-assembling peptide solution. The self-assembling peptide, also referred to herein as "peptide" or "amphiphilic peptide" may be administered, applied, or injected in a solution that is substantially cell-free. In certain embodiments, the self-assembling peptide may be administered, applied, or injected in a solution that is cell-free.

The self-assembling peptide may also be administered, applied or injected in a solution that is substantially drug-free. In certain embodiments, the self-assembling peptide may be administered, applied, or injected in a solution that is drug-free. In certain other embodiments, the self-assembling peptide may be administered, applied, or injected in a solution that is substantially cell-free and substantially drug-free. In still further certain other embodiments, the self-assembling peptide may be administered, applied, or injected in a solution that is cell-free and drug-free.

Administration of a solution may comprise, consist of, or consist essentially of administration of a solution comprising, consisting of, or consisting essentially of an amphiphilic peptide comprising, consisting of, or consisting essentially of at least 12 amino acids that alternate between a hydrophobic amino acid and a hydrophilic amino acid.

The systems and methods may comprise administering a self-assembling peptide to a predetermined or desired target as a hydrogel. A hydrogel is a term that may refer to a colloidal gel that is dispersed in water. The systems and methods may also comprise applying a self-assembling peptide to a predetermined or desired target as a solution, such as an aqueous peptide solution.

When using the term "administering," it is intended to include, but is not limited to, applying, introducing or injecting the self-assembling peptide, in one or more of various forms including, but not limited to, by itself, by way of a solution, such as an aqueous solution, or by way of a hydrogel, with or without additional components.

The method of blocking the biological vessel in a subject may comprise introducing a syringe, pipette, catheter, or other needle-based device into the biological vessel. The self-assembling peptide may be administered by way of a syringe, pipette, catheter, or other needle-based device into the biological vessel. The gauge of the syringe needle may be selected to provide an adequate flow of liquid from the syringe to the target area. This may be based in some embodiments on at least one of the amount of self-assembling peptide or peptide solution being administered, the concentration of the peptide in solution, and the viscosity of the peptide solution.

The method of blocking the biological vessel in the subject may comprise introducing a catheter into the biological vessel and positioning an end of the catheter in a target area of the biological vessel in which at least a partial obstruction is desired. The self-assembling peptide may be administered by way of a catheter to the target area of a biological vessel in which at least a partial obstruction is desired. The use of a catheter may provide a more selective administration of the peptide to provide for a more accurate delivery to the target area. Selective administration of the peptide may allow for enhanced and more targeted delivery of the peptide solution such that blockage of the biological vessel is successful and positioned in the desired location in an accurate manner. The selective administration may provide enhanced, targeted delivery that markedly improves the positioning and effectiveness of the blockage in the biological vessel over use of a syringe or other means.

Use of the catheter may include use of accompanying devices, such as a guidewire used to guide the catheter into position. The guidewire may be introduced into the biological vessel prior to introducing the catheter. Once the administration of the peptide solution is complete, or once the at least partial obstruction or blockage is in place, the catheter may be removed from the biological vessel.

The use of a syringe, needle, pipette, other needle-based device, or catheter may require determining the diameter of the biological vessel which is targeted, such that at least a portion of the syringe, needle, pipette, other needle-type device, or catheter may enter the biological vessel to administer the peptide, peptide solution, or hydrogel to the target area.

In certain embodiments, the hydrogel may be formed in vitro and administered to the desired location in vivo. In certain examples, this location may be the area in which it is desired to create an embolism. In other examples, this location maybe upstream or downstream of the area in which it is desired to form an embolism. In this case, it may be desired to allow an unassisted movement or migration of the hydrogel to the area in which it is desired to form an embolism. Alternatively, another procedure may position the hydrogel in the area in which it is desired to form an embolism. The desired location or target area may be a portion of a biological vessel. The desired location or target area may be a portion within a biological vessel.

In certain aspects of the disclosure, the hydrogel may be formed in vivo. A solution comprising the self-assembling peptide, such as an aqueous solution, may be inserted to an in vivo location or area of a subject to allow an embolism to be created at that location. In certain examples, the hydrogel may be formed in vivo at one location, and allowed to move the hydrogel unassisted to the area in which it is desired to form an embolism. Alternatively, another procedure may place the hydrogel in the area in which it is desired to form an embolism. The peptides of the present disclosure may be in the form of a powder, a solution, a gel, or the like. Since the self-assembling peptide gels in response to changes in solution pH and salt concentration, it can be distributed as a liquid that gels upon contact with a subject during application or administration.

The particular self-assembling peptides of the present disclosure may provide for improved adhesion to tissue over other agents that may be used in biological vessel embolization. The improved adhesion may be due to the composition of the peptide (for example, the particular amino acids of the peptide), the structure of the peptide once self-assembled, or due to the self-assembly process itself. In certain embodiments, it may benefit the procedure to remove excess body fluid, such as blood or bile, from the target site or area in which it is desired to provide a hydrogel for occlusion.

In some embodiments, the peptide or hydrogel may not adhere to the tissue or biological vessel. As the peptide or peptide solution is administered, it comes in contact with the blood or other fluid in the biological vessel, which causes gelation inside the vessel. The peptide solution can move within the vessel, but as it begins to gel it loses its fluidity and will remain in position at a position or target area in the biological vessel. The peptides in the form of a hydrogel may remain in place without adhesion to the tissue or biological vessel.

This disclosure relates to aqueous solutions, hydrogels, and membranes comprising self-assembling peptides, sometimes referred to as self-assembling oligopeptides, or amphiphilic peptides. The peptides may be comprised of an amphiphilic peptide having about 6 to about 200 amino acid residues with the hydrophilic amino acids and hydrophobic amino acids alternately bonded. The self-assembling peptides may exhibit a beta-structure in aqueous solution in the presence of physiological pH and/or a cation, such as a monovalent cation.

The order of effectiveness of the monovalent cations appears to be $Li^+>Na^+>K^+>Cs^+$. $Cs^+$ may produce the least amount of membranes and in addition, yields nonmembranous precipitates. The effectiveness of the monovalent cations may correlate inversely with the crystal radii of the ions: $Li^+$ (0.6 Angstroms), $Na^+$ (0.95 Angstroms), $K^+$ (1.33 Angstroms), and $Cs^+$ (1.69 Angstroms) (Pauling, 1960). A correlation may also be seen with the hydrated radii of the ions: $Li^+$ (3.4 Angstroms), $Na^+$ (2.76 Angstroms), $K^+$ (2.32 Angstroms), and $Cs^+$ (2.28 Angstroms), and with the order of enthalpies of the monovalent cations (Pauling, 1960). The presence of the monovalent metal cations may act as a catalyst or may be incorporated into the membrane. The size of the filaments (10-20 nm) and interfilament distance (50-80 nm) in some membranes formed may suggest that hydrated ions may stabilize the intermolecular interaction. Some anions, including divalent anions, acetate, $Cl^-$, $SO_4^{-2}$, and $PO_4^{-2}$, and organic ions, $NH_4^+$ and Tris-Cl, may not induce membrane formation.

Concentrations of monovalent metal cations (NaCl) as low as 5 mM and as high as 5M have been found to induce membrane formation within a few minutes in certain embodiments. Thus, membrane formation may be independent of salt concentration over this wide range. Salt concentrations of less than 5 mM may also induce membrane formation, but at a slower rate.

The peptides may be generally stable in aqueous solutions and self-assemble into large, extremely stable macroscopic structures or matrices when exposed to physiological conditions or levels of salt. The presence of a monovalent alkali metal ion such as sodium ions and potassium ions present at physiological levels promote formation of a hydrogel from the peptide solution. Once the hydrogel is formed it may not decompose even under common protein denaturing conditions such as high temperature or with denaturing agents such as acids, alkalis, proteases, urea, guanidine hydrochloride or the like. The self-assembled peptides may be visible to the naked eye when stained with a dye, Congo Red, and can form sheet-like or fibril structures which have high tensile strength. These materials are substantially resistant to change in pH, heat, and enzymatic proteolysis. The self-assembled peptides have a fibrous microstructure with small pores as revealed by electron microscopy.

Physiological conditions may occur in nature for a particular organism or cell system, which may be in contrast to artificial laboratory conditions. The conditions may comprise one or more properties such as one or more particular properties or one or more ranges of properties. For example, the physiological conditions may include a temperature or range of temperatures, a pH or range of pH's, a pressure or range of pressures, and one or more concentrations of particular compounds, salts, and other components. For example, in some examples, the physiological conditions may include a temperature in a range of about 20 to about 40 degrees Celsius. In some examples, the atmospheric pressure may be about 1 atm. The pH may be in a range of about 6 to about 8. The physiological conditions may include cations such as monovalent metal cations that may induce membrane formation. These may include sodium chloride (NaCl). The physiological conditions may also include a glucose concentration, sucrose concentration, or other sugar concentration, of between about 1 mM and about 20 mM.

The self-assembling peptides of the present disclosure may have at least 8 amino acids, at least 12 amino acids, or at least 16 amino acids. The peptides may also be complementary and structurally compatible. Complementary refers to the ability of the peptides to interact through ionized pairs and/or hydrogen bonds which form between their hydrophilic side-chains, and structurally compatible refers to the ability of complementary peptides to maintain a constant distance between their peptide backbones. Peptides having these properties participate in intermolecular interactions which result in the formation and stabilization of beta-sheets at the secondary structure level and interwoven filaments at the tertiary structure level.

Both homogeneous and heterogeneous mixtures of peptides characterized by the above-mentioned properties may form stable macroscopic membranes, filaments, and hydrogels. Peptides which are self-complementary and self-compatible may form membranes in a homogeneous mixture. Heterogeneous peptides, including those which cannot form membranes in homogeneous solutions, which are complementary and/or structurally compatible with each other may also self-assemble into macroscopic membranes, filaments, and hydrogels.

Macroscopic membranes, filaments, and hydrogels formed of the self-assembling peptides may be stable in aqueous solution, in serum, and in ethanol, and may be highly resistant to degradation by heat, alkaline and acidic pH (stable at pH 1.5-11), chemical denaturants (for example, guanidine-HCl, urea and sodium dodecyl sulfate), and proteases in vitro (for example, trypsin, alpha-chymotrypsin, papain, protease K, and pronase). They may be non-cytotoxic.

The methods and methods of facilitating of the present disclosure may comprise administering or providing instructions for administering through a catheter a solution comprising an amphiphilic peptide comprising at least 12 amino acids that alternate between a hydrophobic amino acid and a hydrophilic amino acid in an effective amount and in an effective concentration to form a hydrogel under physiological conditions to allow at least partial blockage of a biological vessel.

The methods of facilitating may comprise providing the solution comprising an amphiphilic peptide comprising the at least 12 amino acids that alternate between a hydrophobic amino acid and a hydrophilic amino acid in an effective amount and in an effective concentration to form a hydrogel under physiological conditions to allow at least partial blockage of a biological vessel.

The methods and methods of facilitating may comprise adding a contrast agent to the peptide solution or providing instructions to add a contrast agent to the solution. Alternatively, the peptide solution may be manufactured with a contrast agent. The contrast agent may provide a visual image during use of X-ray techniques, such as fluoroscopy or angiography. A nonionic radiopaque contrast media may be included, such as, for example, a water-soluble iodine based solution. The water-soluble iodine based solution may be iopamidol.

The methods and methods of facilitating of the present disclosure may comprise visualizing a region comprising at least a portion of the biological vessel or providing instructions to visualize a region comprising at least a portion of the biological vessel. The visualization may occur during at least one of identifying the target area, introducing the catheter, positioning the end of the catheter in the target area, administering of the solution, and observing the biological vessel after removing the catheter.

The visualizing may be accomplished through imaging using X-ray radiography. Methods and methods of facilitating may comprise visualizing or providing instructions to visualize the region using X-ray radiography. Visualizing may occur for a period of time after administering the peptide or removing the catheter. For example, it may occur for up to 5 minutes or an hour after administering the peptide or removing the catheter. Visualization may also occur after one or more pre-determined intervals. For example, visualization may occur about 24 hours after administering the peptide or removing the catheter, after about one week, after about two weeks, or after about four weeks. Visualization may occur after about 3 months. Visualization may also occur after 6 months. Instructions may be provided to visualize the region at any one or more of the times disclosed herein and for any period of time. For example, at one week, the visualization may occur for 1 minute or 5 minutes. At four weeks, the visualization may occur for 10 minutes or 3 minutes.

Visualizing or monitoring the area surrounding the formed blockage may also occur for a period of time or at one or more pre-determined intervals after administering the peptide or removing the catheter. This may occur to determine any one or more of the effectiveness of the blockage, any degradation of the blockage, and any cell or tissue necrosis.

The methods of the present disclosure may further comprise evaluating the subject to determine a need for blocking a biological vessel and preparing the peptide solution. Preparing the peptide solution may comprise adding a contrast agent to a preliminary solution comprising peptides.

The method of facilitating may comprise providing instructions to add a contrast agent to the solution. The method of facilitating may comprising providing instructions to combine a sufficient quantity or volume of the contrast agent in order to adequately do at least one of: identify the target area, introduce a catheter or other administration device, position an end of the catheter in the target area, administer the peptide solution, remove the catheter or other administration device, and observe the biological vessel after removing the catheter. The use of the contrast agent may allow visualization of the area to which the peptide, peptide solution or hydrogel is administered.

The amino acids of the self-assembling or amphiphilic peptides may be selected from d-amino acids, 1-amino acids, or combinations thereof. The hydrophobic amino acids include Ala, Val, Ile, Met, Phe, Tyr, Trp, Ser, Thr and Gly. The hydrophilic amino acids can be basic amino acids, for example, Lys, Arg, His, Orn; acidic amino acids, for example, Glu, Asp; or amino acids which form hydrogen bonds, for example, Asn, Gln. Acidic and basic amino acids may be clustered on a peptide. The carboxyl and amino groups of the terminal residues may be protected or not protected. Membranes may be formed in a homogeneous mixture of self-complementary and self-compatible peptides or in a heterogeneous mixture of peptides which are complementary and structurally compatible to each other. Peptides fitting the above criteria may self-assemble into macroscopic membranes under suitable conditions, described herein.

The peptides of the present disclosure may include peptides having the repeating sequence of arginine, alanine, aspartic acid and alanine (Arg-Ala-Asp-Ala (RADA) (SEQ ID NO: 1)), and such peptide sequences may be represented by $(RADA)_p$, wherein p=2-50 (SEQ ID NO: 2). Other peptide sequences may be represented by self-assembling peptides having the repeating sequence of isoleucine, glutamic acid, isoleucine and lysine (Ile-Glu-Ile-Lys (IEIK) (SEQ ID NO: 3)), and such peptide sequences are represented by $(IEIK)_p$, wherein p=2-50 (SEQ ID NO: 4). Other peptide sequences may be represented by self-assembling peptides having the repeating sequence of lysine, leucine, aspartic acid, and leucine (Lys-Leu-Asp-Leu (KLDL) (SEQ ID NO: 5)), and such peptide sequences are represented by $(KLDL)_p$, wherein p=2-50 (SEQ ID NO: 6). The self-assembling peptides may be composed of about 8 to about 200 amino acid residues. In certain embodiments, about 8 to about 32 residues may be used in the self-assembling peptides, while in other embodiments self-assembling peptides may have about 12 to about 17 residues. The peptides may have a length of about 5 nm.

As specific examples of self-assembling peptides according to the invention there may be a self-assembling peptide RADA16 having the sequence Arg-Ala-Asp-Ala-Arg-Ala-Asp-Ala-Arg-Ala-Asp-Ala-Arg-Ala-Asp-Ala (RADA)$_4$ (SEQ ID NO: 7), a self-assembling peptide IEIK13 having the sequence Ile-Glu-Ile-Lys-Ile-Glu-Ile-Lys-Ile-Glu-Ile-Lys-Ile (IEIK)$_3$I (SEQ ID NO: 8), a self-assembling peptide IEIK17 having the sequence Ile-Glu-Ile-Lys-Ile-Glu-Ile-Lys-Ile-Glu-Ile-Lys-Ile-Glu-Ile-Lys-Ile (IEIK)$_4$I (SEQ ID NO: 9) or a self-assembling peptide KLDL12 having the sequence Lys-Leu-Asp-Leu-Lys-Leu-Asp-Leu-Lys-Leu-Asp-Leu (KLDL)$_3$ (SEQ ID NO: 10). A 1% aqueous solution of (RADA)$_4$ (SEQ ID NO: 7) is available as the product PuraMatrix™ by 3D-Matrix Co., Ltd. PuraMatrix™ contains 1% peptide having the sequence (RADA)$_4$ (SEQ ID NO: 7), in water.

Certain peptides may contain sequences which are similar to the cell attachment ligand RGD (Arginine-Glycine-Aspartic acid). The suitability of these peptides for supporting in vitro cell growth was tested by introducing a variety of cultured primary and transformed cells to homopolymer sheets of Ala-Glu-Ala-Glu-Ala-Lys-Ala-Lys-Ala-Glu-Ala-Glu-Ala-Lys-Ala-Lys (AEAEAKAKAEAEAKAK (EAK16) (SEQ ID NO: 11), RAD 16 (SEQ ID NO: 22), RADA16 (SEQ ID NO: 7), and heteropolymers of RAD16 (SEQ ID NO: 22) and EAK16 (SEQ ID NO: 11). The RAD-based peptides may be of particular interest because the similarity of this sequence to RGD. The RAD sequence is a high affinity ligand present in the extracellular matrix protein tenascin and is recognized by integrin receptors. The EAK 16 peptide (SEQ ID NO: 11) and other peptides disclosed herein were derived from a region of a yeast protein, zuotin.

The self-assembly of the peptides may be attributable to hydrogen bonding and hydrophobic bonding between the peptide molecules by the amino acids composing the peptides.

The self-assembling peptides of the present disclosure may have a nanofiber diameter in a range of about 10 nm to about 20 nm and an average pore size is in a range of about 5 nm to about 200 nm. In certain embodiments, the nanofiber diameter, the pore size, and the nanofiber density may be controlled by at least one of the concentration of peptide solution used and the amount of peptide solution used, such as the volume of peptide solution. As such, at least one of a specific concentration of peptide in solution and a specific amount of peptide solution to provide at least one of a desired nanofiber diameter, pore size, and density to adequately deliver and form an embolism upon administration to a biological vessel may be selected.

As used herein, an amount of a peptide, peptide solution or hydrogel effective to provide at least a partial obstruction, blockage, or occlusion or treat a disorder, an "effective amount" or a "therapeutically effective amount" refers to an amount of the peptide, peptide solution or hydrogel, which is effective, upon single or multiple administration (application or injection) to a subject, in treating, or in curing, alleviating, relieving or improving a subject with a disorder beyond that expected in the absence of such treatment. This may include a particular concentration or range of concentrations of peptide in the peptide solution or hydrogel and additionally, or in the alternative, a particular volume or range of volumes of the peptide solution or hydrogel. The method of facilitating may comprise providing instructions to prepare at least one of the effective amount and the effective concentration.

The dosage, for example, volume or concentration, administered (for example, applied or injected) may vary depending upon the form of the peptide (for example, in a peptide solution, hydrogel, or in a dried form, such as a lyophilized form) and the route of administration utilized. The exact formulation, route of administration, volume, and concentration can be chosen in view of the subject's condition and in view of the particular target area or location that the peptide solution, hydrogel, or other form of peptide will be administered. Lower or higher doses than those recited herein may be used or required. Specific dosage and treatment regimens for any particular subject may depend upon a variety of factors, which may include the specific peptide or peptides employed, the dimension of the biological vessel that is being treated or occluded, the desired thickness of the resulting hydrogel that may be positioned in the desired target area, and the length of time of treatment. Other factors that may affect the specific dosage and treatment regimens include age, body weight, general health status, sex, time of administration, rate of degradation, the severity and course of the disease, condition or symptoms, and the judgment of the treating physician. In certain embodiments, the peptide solution may be administered in a single dose. In other embodiments, the peptide solution may be administered in more than one dose, or multiple doses.

An effective amount and an effective concentration of the peptide solution may be selected to at least partially obstruct or block a biological vessel. In some embodiments, at least one of the effective amount and the effective concentration may be based in part on a diameter of the target area of the biological vessel. In other embodiments, at least one of the effective amount and the effective concentration is based in part on the flow rate of the blood in the biological vessel. In other embodiments, at least one of the effective amount and the effective concentration may be based in part on a blood pressure of the blood in the biological vessel. In still other embodiments, at least one of the effective amount and the effective concentration may be based in part on an average diameter of a red blood cell of the subject.

In yet other embodiments, at least one of the effective amount and the effective concentration may be based in part on at least one of the diameter of the target area of the biological vessel, the flow rate of blood in the biological vessel, the blood pressure of the blood in the biological vessel, and the average diameter of a red blood cell of the subject.

The at least one of the effective amount and the effective concentration may be based in part on providing nanofibers of a hydrogel having an average pore size that is less than an average diameter of a red blood cell of the subject. This may comprise collecting a sample of blood from the subject to determine the average red blood cell diameter to provide for the at least one of the effective amount and the effective concentration.

The effective amount may be, as described herein, an amount that may provide for a desired blockage in a biological vessel. Various properties of the biological vessel may contribute to the selection or determination of the effective amount including at least one of the diameter of the target area of the biological vessel, the flow rate of blood in the biological vessel, the blood pressure of the blood in the biological vessel, and the average diameter of a red blood cell of the subject.

The effective amount may include volumes of from about 0.1 milliliters (mL) to about 100 mL of a peptide solution. The effective amount may include volumes of from about 0.1 mL to about 10 mL of a peptide solution. In certain embodiments, the effective amount may be about 0.5 mL. In other embodiments, the effective amount may be about 1.0 mL. In yet other embodiments, the effective amount may be about 1.5 mL. In still yet other embodiments, the effective amount may be about 2.0 mL. In some other embodiments, the effective amount may be about 3.0 mL.

In some embodiments, a more effective blockage may be achieved with a greater volume of peptide solution administered. This may allow a longer or thicker hydrogel to form within the biological vessel, allowing a more secure positon of the hydrogel in the target area. It is possible that if a high enough volume is not selected, the hydrogel may not be effective in maintaining a blockage in the target area for the desired period of time. This may also be influenced based on the blood flow rate or blood pressure in the vessel.

The effective concentration may be, as described herein, an amount that may provide for a desired blockage in a biological vessel. Various properties of the biological vessel may contribute to the selection or determination of the effective concentration including at least one of the diameter of the target area of the biological vessel, the flow rate of blood in the biological vessel, the blood pressure of the blood in the biological vessel, and the average diameter of a red blood cell of the subject.

The effective concentration may include peptide concentrations in the solution in a range of about 0.1 weight per volume (w/v) percent to about 10 w/v percent. The effective concentration may include peptide concentrations in the solution in a range of about 0.1 w/v percent to about 3.5 w/v percent. In certain embodiments, the effective concentration may be about 1 w/v percent. In other embodiments, the effective concentration may be about 2.5 w/v percent. In yet other embodiments, the effective concentration may be about 3.0 w/v percent.

In certain embodiments, a peptide solution having a higher concentration of peptide may provide for a more effective hydrogel that has the ability to stay in place and provide effective blockage of the biological vessel. For purposes of delivering the peptide solution, higher concentrations of peptide solutions may become too viscous to allow for effective and selective administration of the solution. It is possible that if a high enough concentration is not selected, the hydrogel may not be effective in maintaining a blockage in the target area for the desired period of time. This may also be influenced based on the blood flow rate or blood pressure in the vessel.

The effective concentration may be selected to provide for a solution that may be administered by injection or other means using a particular diameter or gauge catheter or needle.

Methods of the disclosure contemplate single as well as multiple administrations of a therapeutically effective amount of the peptides, peptide solutions, and hydrogels as described herein. Peptides as described herein may be administered at regular intervals, depending on the nature, severity and extent of the subject's condition. In some embodiments, a peptide, peptide solution, or hydrogel may be administered in a single administration. In some embodiments, a peptide, peptide solution, or hydrogel described herein is administered in multiple administrations. In some embodiments, a therapeutically effective amount of a peptide, peptide solution, or hydrogel may be administered periodically at regular intervals. The regular intervals selected may be based on any one or more of the initial peptide concentration of the solution administered, the amount administered, and the degradation rate of the hydrogel formed. For example, after an initial administration, a follow-on administration may occur after, for example, two weeks, four weeks, six weeks, or eight weeks. The follow-on administration may comprise administration of a solution having the same concentration of peptide and volume as the initial administration, or may comprise administration of a solution of lesser or great concentration of peptide and volume. The selection of the appropriate follow-on administration of peptide solution may be based on imaging the target area and the area surrounding the target area and ascertaining the needs based on the condition of the subject. The pre-determined intervals may be the same for each follow-on administration, or they may be different. In some embodiments, a peptide, peptide solution, or hydrogel may be administered chronically at pre-determined intervals to maintain at least a partial blockage of a biological vessel in a subject over the life of the subject. The pre-determined intervals may be the same for each follow-on administration, or they may be different. This may be dependent on whether the hydrogel formed from the previous administration is partially or totally disrupted or degraded. The follow-on administration may comprise administration of a solution having the same concentration of peptide and volume as the initial administration, or may comprise administration of a solution of lesser or great concentration of peptide and volume. The selection of the appropriate follow-on administration of peptide solution may be based on imaging the target area and the area surrounding the target area and ascertaining the needs based on the condition of the subject.

The self-assembling peptides of the present disclosure, such as RADA16 (SEQ ID NO: 7), may be peptide sequences that lack a distinct physiologically or biologically active motif or sequence, and therefore may not impair intrinsic cell function. Physiologically active motifs may control numerous intracellular phenomena such as transcription, and the presence of physiologically active motifs may lead to phosphorylation of intracytoplasmic or cell surface proteins by enzymes that recognize the motifs. When a physiologically active motif is present in a peptide tissue occluding agent, transcription of proteins with various functions may be activated or suppressed. The self-assembling peptides, of the present disclosure may lack such physiologically active motifs and therefore do not carry this risk.

A sugar may be added to the self-assembling peptide solution to improve the osmotic pressure of the solution from hypotonicity to isotonicity without reducing the tissue occluding effect, thereby allowing the biological safety to be increased. In certain examples, the sugar may be sucrose or glucose.

In certain embodiments, the peptide length may be more than 12 amino acids and preferably at least 16 residues. Very long peptides, for example, of about 200 amino acids, may encounter problems due to insolubility and intramolecular interactions which destabilize membrane formation, but may also be contemplated herein. Furthermore, peptides with a large amount of hydrophobic residues may have insolubility problems. The optimal lengths for membrane formation may vary with the amino acid composition.

An additional stabilization factor is that complementary peptides maintain a constant distance between the peptide backbones. Peptides which can maintain a constant distance upon pairing are referred to herein as structurally compatible. The interpeptide distance can be calculated for each ionized or hydrogen bonding pair by taking the sum of the number of unbranched atoms on the side-chains of each amino acid in the pair. For example, lysine has 5 and glutamic acid has 4 unbranched atoms on its side-chains, respectively.

Examples of peptides that may form membranes in homogeneous mixtures are shown in Table 1. These examples illustrate some of the variety of amino acid arrangement and composition of membrane-forming peptides.

TABLE 1

Potential membrane-forming peptides

| Name | Sequence (N→C) |
| --- | --- |
| IEIK13 | IEIKIEIKIEIKI (SEQ ID NO: 8) |
| IEIK17 | IEIKIEIKIEIKIEIKI (SEQ ID NO: 9) |
| KAKA16 | KAKAKAKAKAKAKAKA (SEQ ID NO: 12) |
| KAKA5 | KAKAK (SEQ ID NO: 13) |
| KAE16 | AKAKAEAEAKAKAEAE (SEQ ID NO: 14) |
| AKE16 | AKAEAKAEAKAEAKAE (SEQ ID NO: 15) |
| EKA16 | EAKAEAKAEAKAEAKA (SEQ ID NO: 11) |
| EAK8 | AEAEAKAK (SEQ ID NO: 16) |
| EAK12 | AEAKAEAEAKAK (SEQ ID NO: 17) |
| KEA16 | KAEAKAEAKAEAKAEA (SEQ ID NO: 18) |
| AEK16 | AEAKAEAKAEAKAEAK (SEQ ID NO: 19) |
| ARD8 | ARARADAD (SEQ ID NO: 20) |
| DAR16 | ADADARARADADARAR (SEQ ID NO: 21) |
| RAD16 | ARADARADARADARAD (SEQ ID NO: 22) |
| DRA16 | DARADARADARADARA (SEQ ID NO: 23) |
| RADA16 | RADARADARADARADA (SEQ ID NO: 7) |
| ADR16 | ADARADARADARADAR (SEQ ID NO: 24) |
| ARA16 | ARARADADARARADAD (SEQ ID NO: 25) |
| ARDAKE16 | ARADAKAEARADAKAE (SEQ ID NO: 26) |
| AKEW16 | AKAEARADAKAEARAD (SEQ ID NO: 27) |
| ARKADE16 | ARAKADAEARAKADAE (SEQ ID NO: 28) |
| AKRAED16 | AKARAEADAKARADAE (SEQ ID NO: 29) |
| AQ16 | AQAQAQAQAQAQAQAQ (SEQ ID NO: 30) |
| VQ16 | VQVQVQVQVQVQVQVQ (SEQ ID NO: 31) |
| YQ16 | YQYQYQYQYQYQYQYQ (SEQ ID NO: 32) |
| HQ16 | HQHQHQHQHQHQHQHQ (SEQ ID NO: 33) |
| AN16 | ANANANANANANANAN (SEQ ID NO: 34) |
| VN16 | VNVNVNVNVNVNVNVN (SEQ ID NO: 35) |
| YN16 | YNYNYNYNYNYNYNYN (SEQ ID NO: 36) |
| HN16 | HNHNHNHNHNHNHNHN (SEQ ID NO: 37) |
| ANQ16 | ANAQANAQANAQANAQ (SEQ ID NO: 38) |
| AQN16 | AQANAQANAQANAQAN (SEQ ID NO: 39) |
| VNQ16 | VNVQVNVQVNVQVNVQ (SEQ ID NO: 40) |

TABLE 1 -continued

Potential membrane-forming peptides

| Name | Sequence (N→C) |
| --- | --- |
| VQK16 | VQVNVQVNVQVNVQVN (SEQ ID NO: 41) |
| YNQ16 | YNYQYNYQYNYQYNYQ (SEQ ID NO: 42) |
| YQN16 | YQYNYQYNYQYNYQYN (SEQ ID NO: 43) |
| HNQ16 | HNHQHNHQHNHQHNHQ (SEQ ID NO: 44) |
| HQN16 | HQHNHQHNHQHNHQHN (SEQ ID NO: 45) |
| AKQD18 | AKAQADAKAQADAKAQAD (SEQ ID NO: 46) |
| VKQ18 | VKVQVDVKVQVDVKVQVD (SEQ ID NO: 47) |
| YKQ18 | YKYQYDYKYQYDYKYQYD (SEQ ID NO: 48) |
| HKQ18 | HKHQHDHKHQHDHKHQHD (SEQ ID NO: 49) |
| β-Amyloid (1-28) | DAEFRHDSGYEVHHQKLVFFAEDVGSNK (SEQ ID NO: 50) |
| β-Amyloid (25-35) | GSNKGAIIGLM (SEQ ID NO: 51) |
| Substance P | RPKQQFGLM (SEQ ID NO: 52) |
| Spantide | (D)RPKPQQ(D)WF(D)WLL * (SEQ ID NO: 53) |

* (D) in Spantide is a D amino acid incorporated into the peptide

The criteria of amphiphilic sequence, length, complementarity and structural compatibility apply to heterogeneous mixtures of peptides. For example, two different peptides may be used to form the membranes: peptide A, Val-Arg-Val-Arg-Val-Asp-Val-Asp-Val-Arg-Val-Arg-Val-Asp-Val-Asp (VRVRVDVDVRVRVDVD) (SEQ ID NO: 54), as shown in the appended sequence listing), has Arg and Asp as the hydrophilic residues and peptide B, Ala-Asp-Ala-Asp-Ala-Lys-Ala-Lys-Ala-Asp-Ala-Asp-Ala-Lys-Ala-Lys (ADADAKAKADADAKAK) (SEQ ID NO: 55), has Lys and Asp. Peptides A and B are complementary; the Arg on A can form an ionized pair with the Asp on B and the Asp on A can form an ionized pair with the Lys on B. A calculation of the interpeptide distances in such pairs, however, shows that the two peptides are not structurally compatible. Using a conversion factor of 3 Angstroms per atom, the difference in interpeptide distance between the two pairs would be 3 Angstroms. It is estimated that a variation in interpeptide distance of more than 3-4 Angstroms would destabilize intermolecular interactions leading to membrane formation. Thus, in a heterogeneous mixture of peptides A and B, membranes would likely form, but they would be homogeneously composed of either peptide A or B.

Membranes and hydrogels may also be formed of heterogeneous mixtures of peptides, each of which alone would not form membranes, if they are complementary and structurally compatible to each other. For example, mixtures of (Lys-Ala-Lys-Ala)$_4$ (KAKA)$_4$ (SEQ ID NO: 12) and (Glu-Ala-Glu-Ala)$_4$ (EAEA)$_4$ (SEQ ID NO: 56) or of (Lys-Ala-Lys-Ala)$_4$ (KAKA)$_4$ (SEQ ID NO: 12) and (Ala-Asp-Ala-Asp)$_4$ (ADAD)$_4$ (SEQ ID NO: 57) would be expected to form membranes, but not any of these peptides alone due to lack of complementarity.

Peptides, which are not perfectly complementary or structurally compatible, can be thought of as containing mismatches analogous to mismatched base pairs in the hybridization of nucleic acids. Peptides containing mismatches can form membranes if the disruptive force of the mismatched pair is dominated by the overall stability of the interpeptide interaction. Functionally, such peptides can also be considered as complementary or structurally compatible. For example, a mismatched amino acid pair may be tolerated if it is surrounded by several perfectly matched pairs on each side. Mismatched peptides can be tested for ability to self-assemble into macroscopic membranes using the methods described herein.

The peptides can be chemically synthesized or they can be purified from natural and recombinant sources. Using chemically synthesized peptides may allow the peptide solutions to be deficient in unidentified components such as unidentified components derived from the extracellular matrix of another animal. This property therefore may eliminate concerns of infection, including risk of viral infection compared to conventional tissue-derived biomaterials. This may eliminate concerns of infection including infections such as bovine spongiform encephalopathy (BSE), making the peptide highly safe for medical use.

The initial concentration of the peptide may be a factor in the size and thickness of the membrane or hydrogel formed. In general, it may be the case that the higher the peptide concentration, the higher the extent of membrane formation. Membranes or hydrogels may form from initial peptide concentrations as low as about 0.5 mM or about 1 mg/ml (about 0.1 w/v percent). However, membranes or hydrogels formed at higher initial peptide concentrations (about 10 mg/ml (about 1 w/v percent)) may be thicker and thus, likely to be stronger. It may be preferable when producing the membranes or hydrogels to add peptide to a salt solution or a physiological condition, rather than to add salt to a peptide solution.

Formation of the membranes or hydrogels may be very fast, on the order of a few minutes. The formation of the membranes or hydrogels may form instantaneously upon application or injection to a desired area. The formation of the membranes or hydrogels may occur within one to two minutes of application or injection. In other examples, the formation of the membranes or hydrogels may occur within four minutes of application or injection. In certain embodiments the time it takes to form the membranes or hydrogels may be based at least in part on one or more of the concentration of the peptide solution, the volume of peptide solution applied, and the conditions at the area of application or injection (for example, the concentration of monovalent metal cations at the area of application, the blood flow rate, the blood pressure, and the diameter of the biological vessel).

The formation of the membranes or hydrogels may be irreversible. The process may be unaffected by pH of less than or equal to 12 (the peptides tend to precipitate out at pH above 12), and by temperature. The membranes or hydrogels may form at temperatures in the range of 4 to 90 degrees Celsius.

The membranes or hydrogels may remain in position at the target area for a period of time sufficient to provide a desired effect using the methods and kits of the present disclosure. The desired effect may be to reduce or prevent flow of a fluid through a biological pathway or channel. The desired effect may be a blockage, lodging, occlusion, or embolism in one or more biological pathways or channels. The desired effect may be to purposely create such a blockage, lodging or occlusion in order to deprive tumors or other pathological processes of their blood supply (perfusion).

The desired effect using the methods and kits of the present disclosure may be to treat disorders, malformations, or congenital ailments in biological vessels. The desired effect may be to treat one or more of patent ductus arteriosus (PDA), major aortopulmonary collateral artery (MAPCA), recurrent hemotysis, arteriovenous malformations, cerebral aneurysms, gastrointestinal bleeding, epistaxis, post-partum hemorrhage, surgical hemorrhage, and uterine fibroids. The desired effect may include providing at least a partial blockage to produce cell necrosis or to reduce or eliminate cancerous cells.

The period of time that the membranes or hydrogels may remain at the desired area may be for about 10 minutes. In certain examples, it may remain at the desired area for about 35 minutes. In certain further examples, it may remain at the desired area for several days, up to two weeks. In other examples, it may remain at the desired area indefinitely. In other examples, it may remain at the desired area for a longer period of time, until it is naturally degraded or intentionally removed. If the hydrogel naturally degrades over a period of time, subsequent application or injection of the hydrogel to the same or different location in the biological vessel, or another biological vessel may be performed.

In certain embodiments, the self-assembling peptide may be prepared with one or more components that may provide for enhanced effectiveness of the self-assembling peptide or may provide another action, treatment, therapy, or otherwise interact with one or more components of the subject. For example, additional peptides comprising one or more biologically or physiologically active amino acid sequences or motifs may be included as one of the components along with the self-assembling peptide. Other components may include biologically active compounds such as a drug or other treatment that may provide some benefit to the subject. For example, a cancer treating drug or anticancer drug may be administered with the self-assembling peptide, or may be administered separately.

The peptide, peptide solution, or hydrogel may comprise small molecular drugs to treat the subject or to prevent hemolysis, inflammation, and infection. The small molecular drugs may be selected from the group consisting of glucose, saccharose, purified saccharose, lactose, maltose, trehalose, destran, iodine, lysozyme chloride, dimethylisoprpylazulene, tretinoin tocoferil, povidone iodine, alprostadil alfadex, anise alcohol, isoamyl salicylate, $\alpha,\alpha$-dimethylphenylethyl alcohol, bacdanol, helional, sulfazin silver, bucladesine sodium, alprostadil alfadex, gentamycin sulfate, tetracycline hydrochloride, sodium fusidate, mupirocin calcium hydrate and isoamyl benzoate. Other small molecular drugs may be contemplated. Protein-based drugs may be included as a component to be administered, and may include erythropoietin, tissue type plasminogen activator, synthetic hemoglobin and insulin.

A component may be included to protect the peptide solution against rapid or immediate formation into a hydrogel. This may include an encapsulated delivery systems that may degrade over time to allow a controlled time release of the peptide solution into the target area to form the hydrogel over time a desired, predetermined period of time. Biodegradable, biocompatible polymers may be used, such as ethylene vinyl acetate, polyanhydrides, polyglycolic acid, collagen, polyorthoesters, and polylactic acid.

Any of the components described herein may be included in the peptide solution or may be administered separate from the peptide solution. Additionally, any of the methods and methods of facilitating provided herein may be performed by one or more parties.

A peptide, peptide solution, or hydrogel of the disclosure may be provided in a kit. Instructions for administering the solution to a biological vessel in a subject may also be provided in the kit. The peptide solution may comprise an amphiphilic peptide comprising at least 12 amino acids that alternate between a hydrophobic amino acid and a hydrophilic amino acid in an effective amount and in an effective concentration to form a hydrogel under physiological conditions to allow at least partial blockage of a biological vessel. The instructions for administering the solution may comprise methods for administering the peptide, peptide solution, or hydrogel provided herein, for example, by a route of administration described herein, at a dose, volume or concentration, or administration schedule.

The kit may also comprise informational material. The informational material may be descriptive, instructional, marketing or other material that relates to the methods described herein. In one embodiment, the informational material may include information about production of the peptide, peptide solution, or hydrogel disclosed herein, physical properties of the peptide, peptide solution or hydrogel, concentration, volume, size, dimensions, date of expiration, and batch or production site.

The kit may also optionally include a device or materials to allow for administration of the peptide or peptide solution to the desired area. For example, a syringe, pipette, catheter, or other needle-based device may be included in the kit. Additionally, or alternatively, the kit may include a guidewire or other accompanying equipment to provide selective administration of the peptide solution to the target area.

The kit may comprise in addition to or in the alternative, other components or ingredients, such as components that may aid in contrast imaging. For example, the kit may comprise a contrast agent. The contrast agent may provide a visual image during use of X-ray techniques, such as fluoroscopy or angiography. A nonionic radiopaque contrast media may be included, such as, for example, a water-soluble iodine based solution. The water-soluble iodine based solution may be iopamidol. Instructions may be provided in the kit to combine a sufficient quantity or volume of the contrast agent in order to adequately do at least one of: identify the target area, introduce a catheter or other administration device, position an end of the catheter in the target area, administer the peptide solution, remove the catheter or other administration device, and observe the biological vessel after removing the catheter. The use of the contrast agent may allow visualization of the area to which the peptide, peptide solution or hydrogel is administered. Instructions may be provided for diluting the peptide solution to administer an effective concentration of the solution to the biological vessel. Instructions may further be provided for determining at least one of the effective concentration of the solution and the effective amount of the solution to the biological vessel. This may be based on various parameters discussed herein, and may include the diameter of the biological vessel at the target area.

Other components or ingredients may be included in the kit, in the same or different compositions or containers than the peptide, peptide solutions, or hydrogel. The one or more components that may include components that may provide for enhanced effectiveness of the self-assembling peptide or may provide another action, treatment, therapy, or otherwise interact with one or more components of the subject. For example, additional peptides comprising one or more biologically or physiologically active sequences or motifs may be included as one of the components along with the self-assembling peptide. Other components may include biologically active compounds such as a drug or other treatment that may provide some benefit to the subject. For example, a cancer treating drug or anticancer drug may be administered with the self-assembling peptide, or may be administered separately. The peptide, peptide solution, or hydrogel may comprise small molecular drugs to treat the subject or to prevent hemolysis, inflammation, and infection, as disclosed herein. A sugar solution such as a sucrose solution may be provided with the kit. The sucrose solution may be a 20% sucrose solution.

Other components which are disclosed herein may also be included in the kit.

In some embodiments, a component of the kit is stored in a sealed vial, for example, with a rubber or silicone closure (for example, a polybutadiene or polyisoprene closure). In some embodiments, a component of the kit is stored under inert conditions (for example, under nitrogen or another inert gas such as argon). In some embodiments, a component of the kit is stored under anhydrous conditions (for example, with a desiccant). In some embodiments, a component of the kit is stored in a light blocking container such as an amber vial.

As part of the kit or separate from a kit, syringes or pipettes may be pre-filled with a peptide, peptide solution, or hydrogel as disclosed herein. Methods to instruct a user to supply a self-assembling peptide solution to a syringe or pipette, with or without the use of other devices, and administering it to the target area through the syringe or pipette, with or without the use of other devices, is provided. Other devices may include, for example, a catheter with or without a guidewire.

In some embodiments of the disclosure, the self-assembling peptides may be used as a coating on a device or an instrument such as a stent or catheter, to suppress body fluid leakage. The self-assembling peptides may also be incorporated or secured to a support, such as gauze or a bandage, or a lining, that may provide a therapeutic effect to a subject, or that may be applied within a biological vessel. The self-assembling peptides may also be soaked into a sponge for use.

In alternative embodiments, an atomizing sprayer filled with a powder or solution of the self-assembling peptides may be prepared. When such a spray is used for spraying onto an affected area, the pH and salt concentration increase upon contact with the body causing gelling.

Modification of the membranes may give them additional properties. For example, the membranes may be further strengthened by cross-linking the peptides after membrane formation by standard methods. Collagen may be combined with the peptides to produce membranes more suitable for use as artificial skin; the collagen may be stabilized from proteolytic digestion within the membrane. Furthermore, combining phospholipids with the peptides may produce vesicles.

The membranes may also be useful for culturing cell monolayers. Cells prefer to adhere to non-uniform, charged surfaces. The charged residues and conformation of the proteinaceous membranes promote cell adhesion and migration. The addition of growth factors, such as fibroblast growth factor, to the peptide membrane can further improve attachment, cell growth and neurite outgrowth.

The function and advantage of these and other embodiments of the methods and kits disclosed herein will be more fully understood from the example below. The following example is intended to illustrate the benefits of the disclosed treatment approach, but do not exemplify the full scope thereof.

EXAMPLES

Example 1

Tests were performed on a rat using a 3% (weight per volume (w/v)) PuraMatrix™ solution, a peptide solution comprising Ac-RADARADARADARADA-NH₂ (Ac-Arg-Ala-Asp-Ala-Arg-Ala-Asp-Ala-Arg-Ala-Asp-Ala-Arg-Ala-Asp-Ala-NH₂) (SEQ ID NO: 58) in water. An 18 gauge needle was used to inject 1 milliliter (mL) into a rat portal vein. Hematoxylin-Eosin (HE) dye was used to implement a histopathological evaluation. It was confirmed that an embolism developed in the portal vein using the peptide solution. As shown in FIG. 1, the peptide solution appears to have developed into a hydrogel 2 and resides in the rat portal vein. A red blood cell 4 is also shown.

Example 2

Tests were performed in two beagles using a 2.5% PuraMatrix™ solution, a peptide solution comprising Ac-RADARADARADARADA-NH₂ (Ac-Arg-Ala-Asp-Ala-Arg-Ala-Asp-Ala-Arg-Ala-Asp-Ala-Arg-Ala-Asp-Ala-NH₂) (SEQ ID NO: 58) in water. These tests were performed to confirm the effectiveness of beagle hepatic artery embolism and hepatic cell necrosis using the 2.5% peptide solution. The peptide solution included iopamidol at a concentration of 612.4 mg/mL. Iopamidol is a nonionic radiopaque contrast agent.

Under X-ray imaging of a beagle under full anesthesia, a microcatheter (Terumo, minimum inner diameter of 0.50 mm) was inserted by way of the carotid artery into the hepatic artery. Hepatic artery contrast imaging was used to confirm that the hepatic artery was operational. A 2 mL volume of the 2.5% peptide solution (with Iopamidol) was injected.

Figure 2:
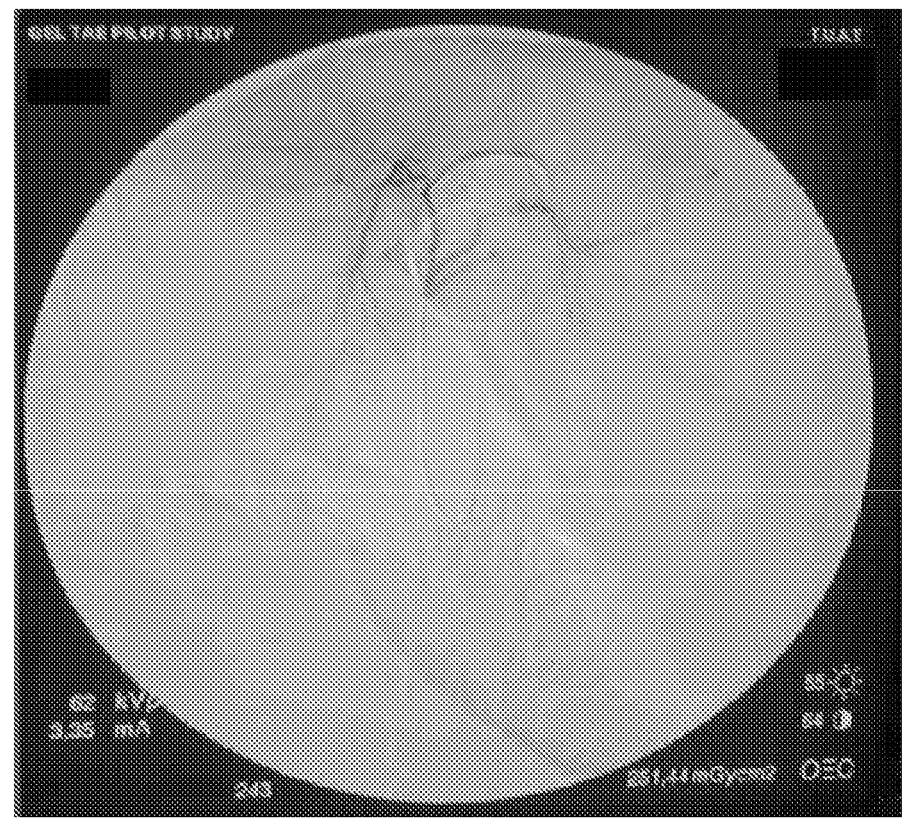
FIG. 2 is a contrast image of a normal hepatic artery.
Figure 3:
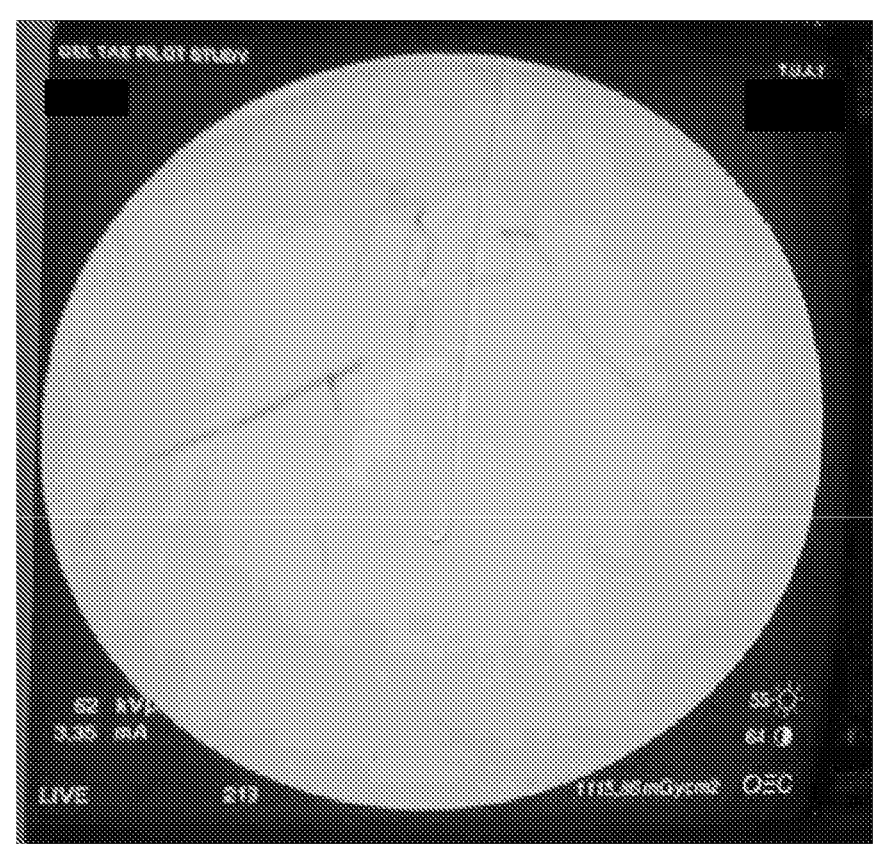
FIG. 3 is a contrast image of an injection of the materials of the present disclosure.
Figure 4:
FIG. 4 is a contrast image of a hepatic artery after injection with the materials of the present disclosure.

Hepatic artery contrast imaging was used to confirm the hepatic artery peptide solution embolism effect during surgery. FIG. 2 displays a contrast image of a normal hepatic artery of the beagle, while FIG. 3 shows the peptide solution injection. FIG. 4 shows a hepatic artery contrast image after a peptide solution injection in which back flow of the contrast image was confirmed. The presence of the peptide solution is evidenced by the darker regions of the image.

Figure 5:
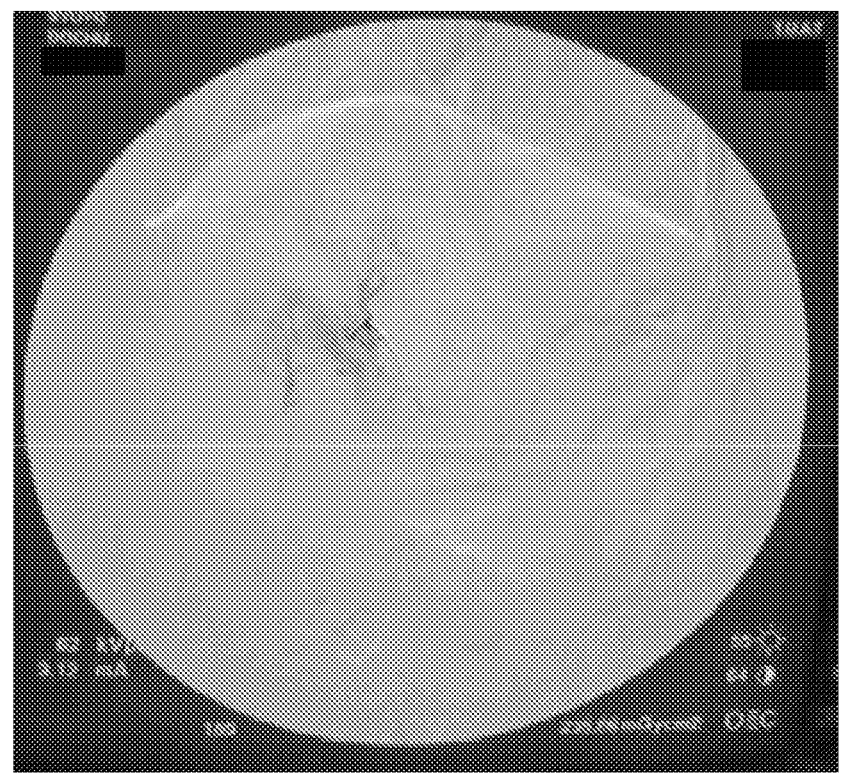
FIG. 5 is a contrast image of a hepatic artery two weeks after injection with the materials of the present disclosure.

After two weeks of monitoring elapsed, hepatic artery contrast imaging was used to confirm the embolism effect. FIG. 5 shows a hepatic artery contrast image two weeks after a peptide solution injection.

Figure 6A:
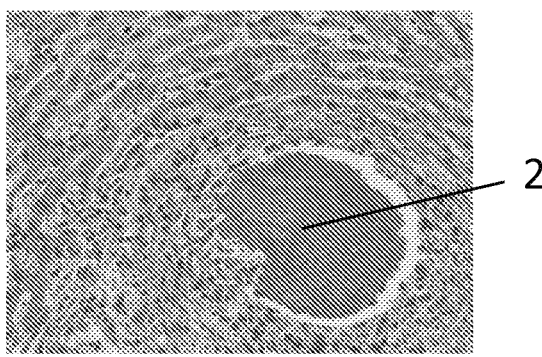
FIG. 6A is a histopathological image of a peptide hydrogel located in a hepatic artery.
Figure 6B:
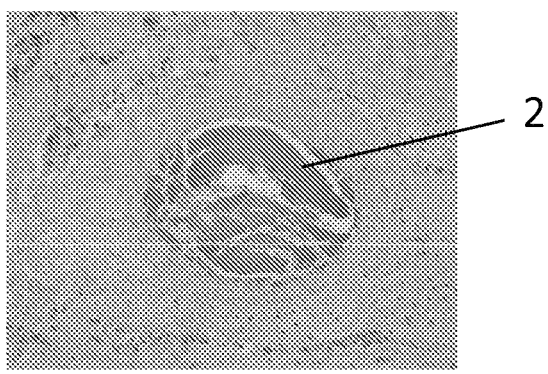
FIG. 6B is a histopathological image of peptide hydrogel located in a hepatic artery.
Figure 6C:
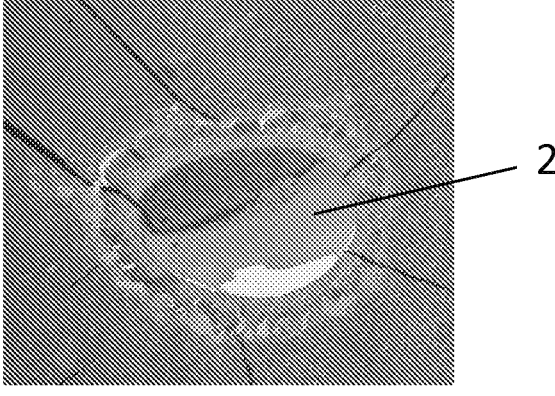
FIG. 6C is a histopathological image of peptide hydrogel located in a hepatic artery.
Figure 7:
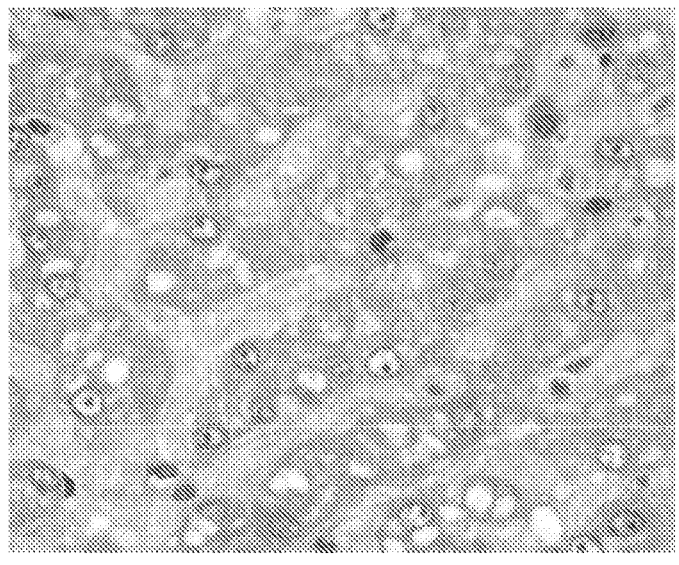
FIG. 7 is a hepatic cell necrosis image of a peptide hydrogel embolism location.

Subsequently, the liver was extracted. Hematoxylin-Eosin (HE) dye was used to histopathologically confirm the peptide solution embolism and hepatic impairment. As shown in FIGS. 6A-6C, the peptide solution can be seen in each of these images of the hepatic artery as the darkened areas of the images. FIG. 7 shows a hepatic cell necrosis image at an embolism location, where all cells appear to have at least some level of necrosis.

The results show that injection of the peptide solution using a microcatheter may be accomplished. The peptide gel may be visible using X-ray imaging. The hepatic artery embolism effect can be seen during surgery and two weeks after surgery. Additionally, the hepatic artery embolism effect and hepatic cell necrosis effect using the peptide solution occurred and was confirmed histopathologically.

Example 3

PuraMatrix™, a peptide solution comprising Ac-RADARADARADARADA-NH₂ (Ac-Arg-Ala-Asp-Ala-Arg-Ala-Asp-Ala-Arg-Ala-Asp-Ala-Arg-Ala-Asp-Ala-NH₂) (SEQ ID NO: 58) in water was used as an embolic agent in a porcine model through angiography, gross necropsy assessment, and histopathology assessment. One female Yorkshire cross swine was tested. The weight of the swine at the time of testing was 46.5 kg. Feed and water were provided per standard operating procedures. There were no contaminants in the food or water that were expected to interfere with the conduct or results of the study. The swine was acquired from a test facility approved animal supplier. The Swine participated in an incoming physical exam, and after a period of acclimation was again examined. The swine was fasted a minimum of 12 hours prior to the procedures. The animals were sedated and anesthetized by an intramuscular or subcutaneous injection of Telazol (2-10 mg/kg) and Xylazine (0.5=5.0 mg/kg). Propofol (to effect) was given to aid in sedation. An endotracheal tube was used to ensure proper ventilation and the animals were maintained under general anesthesia with inhalant isofluorante (0.1 to 5.0%). Heparin (50-300 units/kg, IV) was administered throughout the procedure.

A 2.5% test solution of the peptide solution was used. Approximately 800 microliters of the peptide solution was placed in an eppendorf tube. Approximately 200 microliters of Isovue-370 (Iopamidol) contrast agent was added. The liquids were mixed slowly so as to not create air bubbles.

Figure 8:
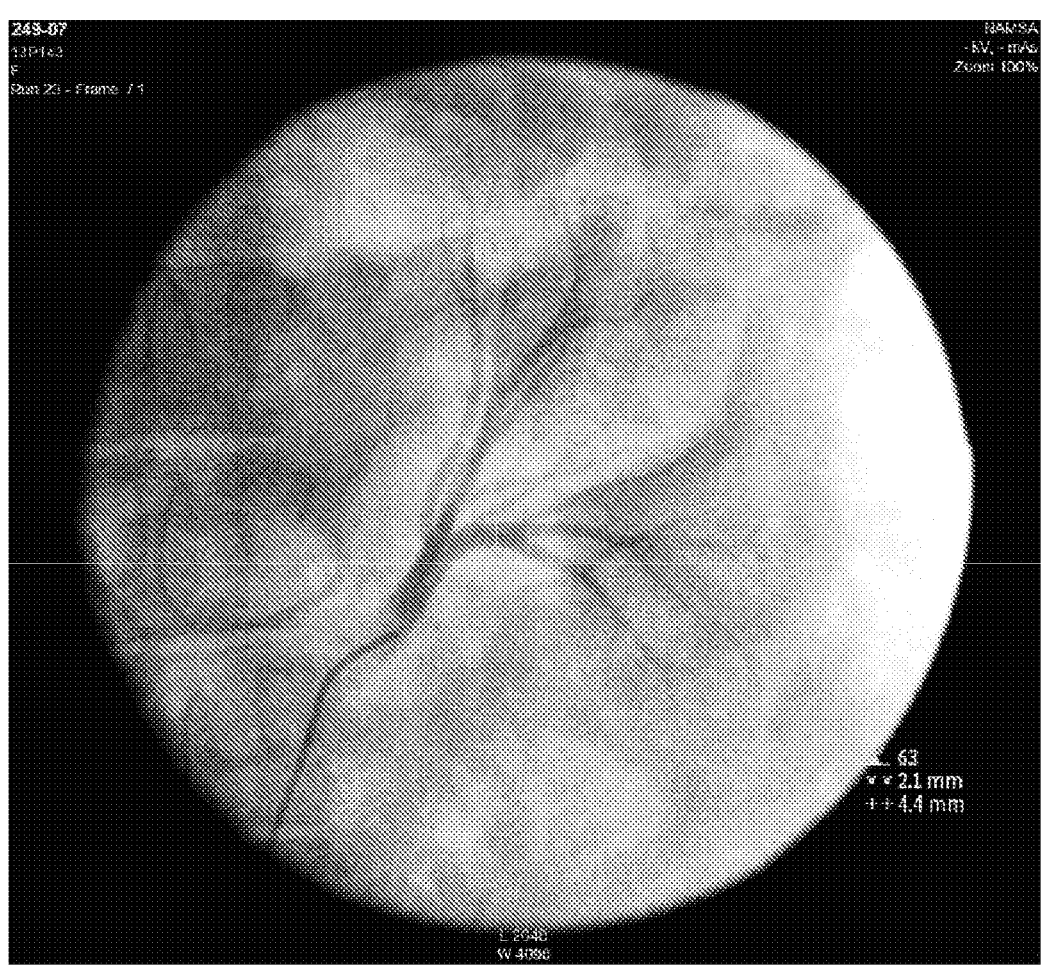
FIG. 8 is an image of an artery before embolization.
Figure 9:
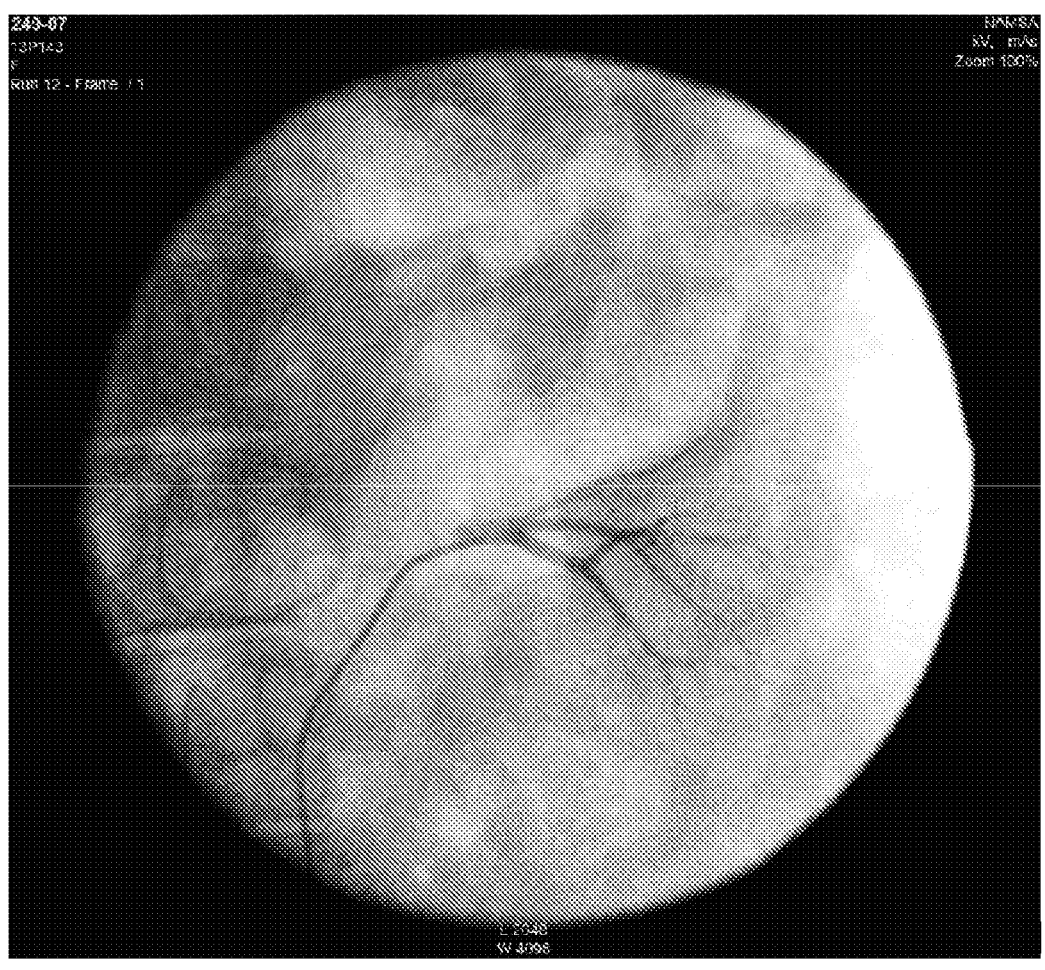
FIG. 9 is an image of an artery after embolization.

On the day of testing, the swine was 2 months, 25 days old. The swine was sedated and prepared for surgery. The femoral artery was accessed and an introducer was placed. A guidewire was advanced to the selected renal artery. A catheter was advanced to the selected renal artery. Angiography was used to visualize the location within the artery. The peptide solution was injected to the desired location until the artery was occluded. This procedure was repeated in the hepatic and splenic arteries. Angiography was used throughout the procedure to visualize the vessels and devices throughout testing. FIGS. 8 and 9 are representative examples of a vessel before (FIG. 6) and after (FIG. 9) embolization. There were no adverse events reported throughout the testing.

A summary of the data can be found in Table 2 below.

TABLE 2

| Test Number | Site | Embolization Time | Approximate Volume Placed | Comments |
|---|---|---|---|---|
| 1 | Left Kidney Renal Artery | Start 13:55 | 1.5 mL | Successful embolization immediately following injection of peptide solution/Isovue |
| 2 | Right Kidney Renal Artery | Start 14:12 | 1.5 mL | Successful embolization immediately following injection. Slight flow reestablished at 14:18. Additional PuraMatrix ™/ Iopamidol placed at 14:27. Angiogram showed full occlusion. |

TABLE 2-continued

| Test Number | Site | Embolization Time | Approximate Volume Placed | Comments |
|---|---|---|---|---|
| 3 | Hepatic Artery | Start 14:58 | 2.0 mL | Successful embolization immediately following injection. At 15:08, the artery remained occluded. At 15:32, the artery remained occluded. |
| 4 | Splenic Artery | Start 15:17 | 3.0 mL | Vessel was completed occluded at 15:21. |

As shown in Table 2, injection into the left kidney renal artery was successful, immediately following injection. Successful embolization of the right kidney renal artery was successful immediately following injection, however, a slight flow was reestablished 6 minutes after the initial injection. An additional injection was made 15 minutes after the initial injection, and a full occlusion was obtained.

Successful embolization of the hepatic artery was also obtained immediately following injection. The artery remained occluded after 10 minutes and 34 minutes. Successful embolization of the splenic artery was also obtained after four minutes.

The description and figures provided are for example only and are not intended to be limiting. While exemplary embodiments of the disclosure have been disclosed many modifications, additions, and deletions may be made therein without departing from the spirit and scope of the disclosure and its equivalents, as set forth in the following claims.

Those skilled in the art would readily appreciate that the various configurations described herein are meant to be exemplary and that actual configurations will depend upon the specific application for which the system and methods of the present disclosure are used. Those skilled in the art will recognize, or be able to ascertain using no more than routine experimentation, many equivalents to the specific embodiments described herein.

Further, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only. Further, the depictions in the drawings do not limit the disclosures to the particularly illustrated representations.

As used herein, the terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The invention claimed is:

1. A method for reducing or eliminating cancerous cells in a subject by forming at least a partial blockage, lodging, occlusion, or embolism in a targeted biological vessel in which blood is flowing, to deprive a tumor in the subject of blood supply, or for treating patent ductus arteriosus (PDA) or major aortopulmonary collateral artery (MAPCA), in a human subject, the method comprising:

administering a solution comprising an amphiphilic self-assembling peptide having the amino acid sequence IEIKIEIKIEIKI (SEQ ID NO:8) in an effective amount and in an effective concentration to form a hydrogel under physiological conditions to provide at least partial blockage of the biological vessel effecting embolization or cell necrosis therein, wherein the concentration effective to provide at least partial blockage of the biological vessel comprises a concentration within the range of 0.1 weight per volume (w/v) percent to 3 w/v percent peptide.

2. The method of claim 1, wherein the peptide solution comprises a contrast agent.

3. The method of claim 1, wherein at least one of the effective amount and the effective concentration is based in part on a diameter of the target area of the biological vessel.

4. The method of claim 1, wherein at least one of the effective amount and the effective concentration is based in part on the flow rate of the blood in the targeted area of the biological vessel.

5. The method of claim 1, wherein at least one of the effective amount and the effective concentration is based in part on providing nanofibers of the hydrogel having an average pore size that is less than an average diameter of a red blood cell of the subject.

6. The method of claim 1, wherein the amount effective to allow at least partial blockage of the biological vessel comprises a volume in a range of about 0.1 mL to about 5 mL.

7. The method of claim 1, wherein the peptide solution is free of cells and/or drugs.

8. The method of claim 1, wherein the solution is provided in a single dose; or the solution is provided in at least two doses.

9. The method of claim 1, wherein administration of the solution provides complete blockage of the targeted biological vessel.

* * * * *